(12) United States Patent
Chiang et al.

(10) Patent No.: US 9,211,244 B2
(45) Date of Patent: Dec. 15, 2015

(54) METHOD FOR ANTI-SKIN AGING USING CAFFEAMIDE DERIVATIVE

(71) Applicant: CHINA MEDICAL UNIVERSITY, Taichung (TW)

(72) Inventors: Hsiu-Mei Chiang, Taichung (TW); Yueh-Hsiung Kuo, Taichung (TW); Kuo-Ching Wen, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 14/048,847

(22) Filed: Oct. 8, 2013

(65) Prior Publication Data

US 2015/0010484 A1 Jan. 8, 2015

(30) Foreign Application Priority Data

Jul. 8, 2013 (TW) .............................. 102124358 A

(51) Int. Cl.
| | | |
|---|---|---|
| A61K 8/42 | (2006.01) | |
| A61Q 19/08 | (2006.01) | |
| A61Q 19/02 | (2006.01) | |
| A61K 8/49 | (2006.01) | |
| A61K 8/69 | (2006.01) | |

(52) U.S. Cl.
CPC ................ *A61K 8/42* (2013.01); *A61K 8/4913* (2013.01); *A61K 8/4926* (2013.01); *A61K 8/69* (2013.01); *A61Q 19/02* (2013.01); *A61Q 19/08* (2013.01); *A61K 2800/522* (2013.01)

(58) Field of Classification Search
CPC ..... A61K 8/42; A61K 8/4913; A61K 8/4926; A61Q 19/08; A61Q 19/02
See application file for complete search history.

(56) References Cited

U.S. PATENT DOCUMENTS

2014/0045777 A1 2/2014 Potin et al.

FOREIGN PATENT DOCUMENTS

| EP | 0 935 963 A2 | | 8/1999 |
|---|---|---|---|
| FR | 2708851 | * | 8/1995 |
| WO | WO 02/19982 | * | 3/2002 |

OTHER PUBLICATIONS

Shi, Z-H. et al. Design, Synthesis and Biological Evaluation of Caffeic Acid Amides as Selective MMP-2 and MMP-9 Inhibitors, Drug Development Research, 2012, 73, 343-351 (published online on Sep. 14, 2012).*

Machine English translation of FR 2708851; obtained on Aug. 21, 2015.*

Veronique Le Mellay-Hamon, et al., "Phenylethylamide and Phenylmethylamide Derivatives as New Tyrosinase Inhibitors", Biol. Pharm. Bull. 32(2) pp. 301-303 (2009).

Yang Yang, et al., "Synthesis and antioxidant capacities of hydroxyl derivatives of cinnamoylphenethylamine in protecting DNA and scavenging radicals", Free Radical Research, Apr. 2011; 45 (4), 2010, pp. 445-453.

Zhi-Hao Shi, et al., "Synthesis and structure-activity relationship analysis of caffeic acid amides as selective matrix metalloproteinase inhibitors", Bioorganic & Medicinal Chemistry Letters, 23 (2013), pp. 1206-1211.

J.P. Ley, "Phenolic acid amides of phenolic benzylamines against UVA-induced oxidative stress in skin", International Journal of Cosmetic Science, 23, 2001, pp. 35-48.

Dorecka, M. et al., "The influence of elastin degradation products, glucose and atorvastatin on metalloproteinase-1, -2, -9 and tissue inhibitor of metalloproteinases-1, -2, -3 expression in human retinal pigment epithelial cells", Acta Biochim Pol., 2014, vol. 61(2), pp. 265-270.

Lee, S. H. et al., "Mulberroside F isolated from the leaves of Morus alba inhibits melanin biosynthesis", Biol. Pharm. Bull., Aug. 2002; vol. 25(8), pp. 1045-1048.

* cited by examiner

*Primary Examiner* — Johann R Richter
*Assistant Examiner* — Genevieve S Alley
(74) *Attorney, Agent, or Firm* — Ping Wang; Andrews Kurth LLP

(57) ABSTRACT

A method for anti-skin aging, especially for anti-skin photoaging in a subject is provided. The method comprising administering to the subject an effective amount of an active component selected from the group consisting of a caffeamide derivative of formula (I), a pharmaceutically acceptable salt of the caffeamide derivative, and a combination thereof:

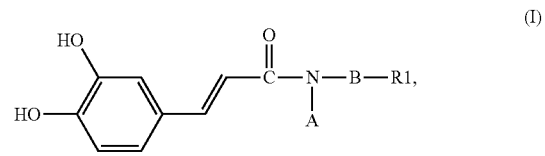

(I)

wherein A is H or an alkyl; B is —$[CH_2]_m$—; m is an integer ranging from 0 to 10; R1 is H, an optionally substituted phenyl, an optionally substituted pyridyl, —OH, or —$OCH_3$; or, N, A, B, and R1 together form an optionally substituted pyrrolyl or piperidyl.

8 Claims, 17 Drawing Sheets
(2 of 17 Drawing Sheet(s) Filed in Color)

(a)

(b)

(a)

(b)

(a)

(b)

(c)

(d)

(e)

(f)

(g)

(h)

(i)

(j)

(a)

(b)

(a)

(b)

METHOD FOR ANTI-SKIN AGING USING CAFFEAMIDE DERIVATIVE

This application claims priority from Taiwan Patent Application No. 102124358 filed on Jul. 8, 2013, with the Taiwan Intellectual Property Office. The entirety of the aforementioned application is incorporated herein by reference.

FIELD

The present invention relates to a method for anti-skin aging, especially for anti-skin photo-aging, by using a caffeamide derivative and/or a pharmaceutically acceptable salt thereof. In particular, the method of the present invention is for anti-oxidation, inhibiting the activity and/or expression of matrix metalloproteinase (MMP), inhibiting the phosphorylation of mitogen-activated protein kinase (MAPK), promoting the expression of collagen, inhibiting the activity and/or expression of tyrosinase, inhibiting the expression of tyrosinase related protein-1 and/or tyrosinase related protein-2, and/or absorbing ultraviolet (UV) rays with a wavelength ranging from 210 nm to 400 nm.

BACKGROUND OF THE INVENTION

Collagen is the main component for maintaining the elasticity of the skin and muscle. Animal collagen that is currently known can be classified approximately into 21 types. Different kinds of collagen exist in different tissues. Out of all collagen in the skin, Type I collagen is the most abundant and has the most functions. Type I collagen accounts for about 80% of the skin collagen, and Type III collagen accounts for about 20% of the skin collagen. Fibroblasts in the dermis mainly produce Type I collagen and Type III collagen for the skin.

The layers of the skin from top to bottom are the epidermis, dermis, and hypodermis. Natural human aging processes include skin flaccidity, wrinkle formation and skin darkening, which gradually appear with aging. The causes of skin aging can be classified into endogenous and exogenous factors. Endogenous aging is a natural aging process of the human body caused by increasing age, decreasing hormone levels, and a weakened immunity. Exogenous aging is caused by extrinsic factors, such as sunshine, pollution, free radical damage, and smoking.

In general, all of the causes of endogenous and exogenous aging can promote the phosphorylation of the MAPK pathway, thereby, increasing the content of MMP in the dermis. MMP may decompose collagen and reduce the content of the collagen in the skin. Without the support of collagen, the skin becomes flaccid and the stratum corneum thickens, leading to darkened and wrinkled skin. In addition, reactive oxygen species (ROS) in cells, such as the organic and inorganic substances of superoxide anions, peroxides and free radicals may also cause the denaturation of collagen and the loss of function of collagen.

Another characteristic of skin aging is the accumulation of melanin in the skin, which causes darkened skin and/or dark spots. Melanin is produced by the basal melanocytes presented in the bottom layer of the epidermis of the skin. The melanogenesis is initiated by the binding of α-melanocyte stimulating hormone (α-MSH) secreted by the keratinocytes in the skin to melanocortin 1 receptor (MC1R) on melanocytes, to activate the cAMP pathway in the melanocytes. The tyrosinase in the melanocytes then activates and catalyzes the conversion of tyrosine to dopaquinone. Dopaquinone can be further converted to melanin through a series of biochemical reactions under the catalysis of tyrosinase related protein-1 (TRP-1) and tyrosinase related protein-2 (TRP-2).

Among all causes of skin aging, UV rays from the sun are the most damaging and significantly accelerate skin aging. Depending on the wavelength, UV rays can be classified into long wavelength UV (UVA) with a wavelength ranging from 320 nm to 400 nm, medium wavelength UV (UVB) with a wavelength ranging from 275 nm to 320 nm, and short wavelength UV (UVC) with a wavelength ranging from 200 nm to 275 nm. The primary UV rays that people are exposed to in daily life are UVA and UVB. Long term exposure of UVA and UVB may cause erythema, sunburns, damage to the deoxyribonucleic acid (DNA) in skin cells, abnormality of the skin immune system, and skin cancer.

The aging phenomenon caused by UV rays is called as "photo-aging," which may promote the production of ROS and activate the MAPK pathway in cells, thereby increasing the content of MMPs, and leading to the decomposition of the collagen in the skin. In addition, UV rays irradiation may promote the melanogenesis of melanocytes, which causes the accumulation of melanin in the skin. Therefore, if the UV rays which the skin is exposed to can be blocked (such as by absorbing the UV rays which irradiate the epidermis of the skin, thereby, reducing the UV rays which penetrate the epidermis of the skin), the MAPK pathway in the cells can be inhibited, the activity and/or expression of MMPs can be inhibited, and/or the melanogenesis can be inhibited, the effects of improving/caring for skin quality and anti-skin aging can be achieved.

Previous studies found that ziyuglycoside-I extracted from the root of *Sanguisorba officinalis* by 70% ethanol can inhibit the expression of MMP-1. In addition, sumaflavone and amentoflavone extracted from *Selaginella tamariscina* by methanol can inhibit the expression of MMP-1. However, there is still a great need for a component which can inhibit the activity of MMPs and has a better effect of anti-aging.

The inventors of the present invention found that the compound of formula (I) of the present invention has excellent effects of anti-oxidation, inhibiting the activity and/or expression of MMPs, inhibiting the phosphorylation of mitogen-activated protein kinases (MAPKs), promoting the expression of collagen, inhibiting the activity and/or expression of tyrosinase, inhibiting the expression of tyrosinase related protein-1 and/or tyrosinase related protein-2, and/or absorbing UV rays with a wavelength ranging from 210 nm to 400 nm, so as to alleviate/prevent the decomposition and/or denaturation of collagen and inhibit melanogenesis, and thus, can be used for anti-skin aging.

SUMMARY OF THE INVENTION

An objective of the present invention is to provide a method for anti-skin aging, especially for anti-skin photo-aging in a subject, comprising administering to the subject an effective amount of an active component selected from the group consisting of a coffeamide derivative of formula (I), a pharmaceutically acceptable salt of the caffeamide derivative, and a combination thereof:

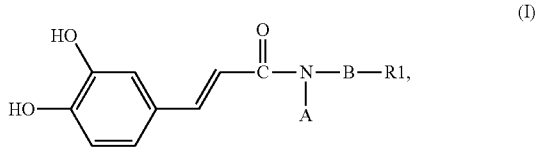

wherein A is H or an alkyl; B is —[CH$_2$]$_m$—; m is an integer ranging from 0 to 10; R1 is H, an optionally substituted phenyl, an optionally substituted pyridyl, —OH, or —OCH$_3$; or N, A, B, and R$_1$ together form an optionally substituted pyrrolyl or piperidyl.

Another objective of the present invention is to provide a method for improving, caring, and/or repairing the skin of a subject, comprising administering to the subject an effective amount of an active component selected from the group consisting of a caffeamide derivative of formula (I), a pharmaceutically acceptable salt of the caffeamide derivative, and a combination thereof.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

DESCRIPTION OF THE PREFERRED EMBODIMENT

Figure 1:
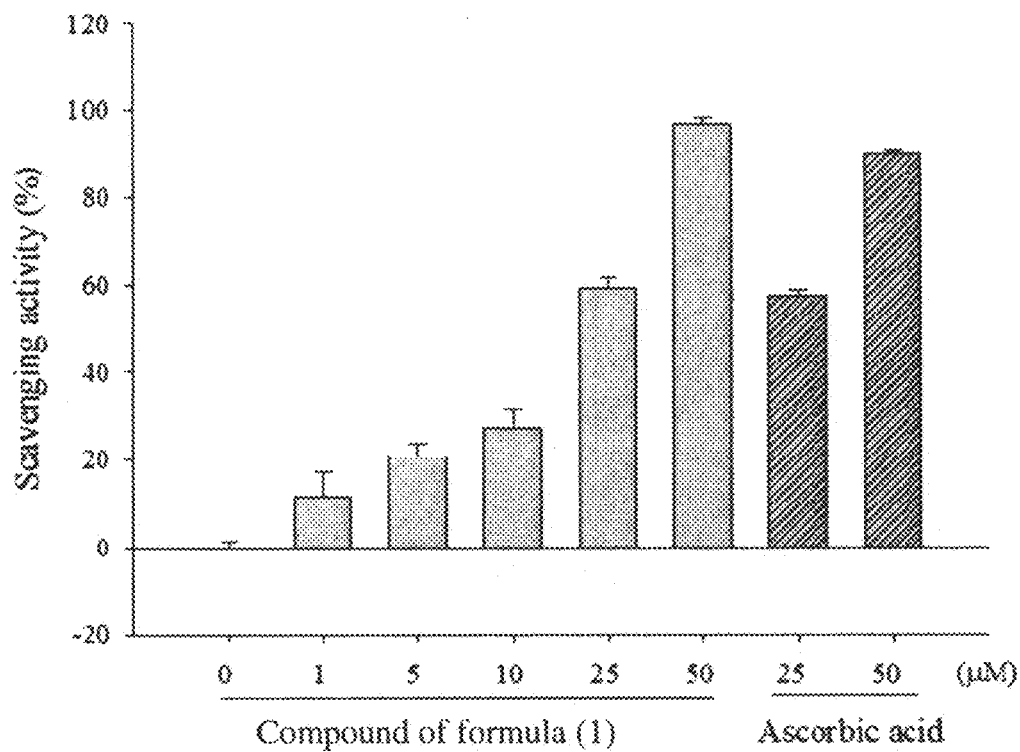
FIGS. 1a and 1b are statistical bar diagrams showing the scavenging efficiency of the caffeamide derivatives of the present invention on DPPH free radicals.
Figure 1:
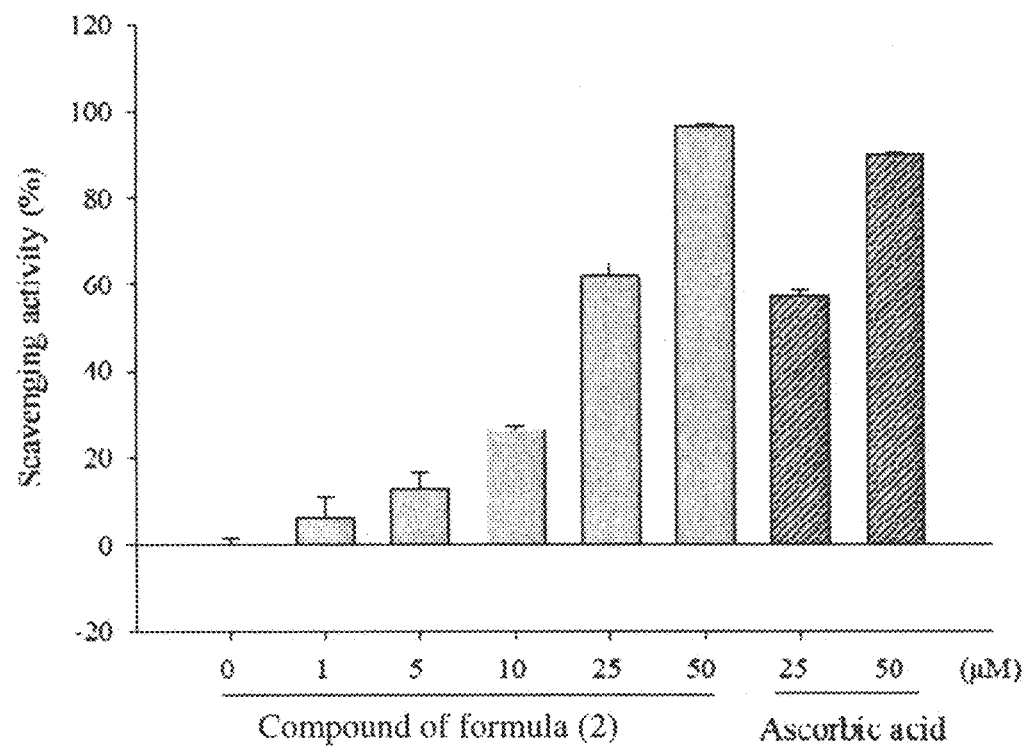

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the," or the like recited in the specification of the present invention (especially in the claims) should include both the singular and plural forms. Furthermore, the term "effective amount" used in this specification refers to the amount of the compound that can at least partially alleviate the condition that is being treated in a suspected subject when administered to the subject. The term "subject" used in this specification refers to a mammalian, including human and non-human animals.

As described above, the primary mechanism for inducing skin aging includes: (1) over activation of the phosphorylation of MAPK pathway, which may increase the content of MMPs in the dermis, cause denaturation or decomposition of collagen, and lead to skin wrinkles and skin flaccidity; and (2) over activation of melanogenesis, which may result in over accumulation of melanin in the skin, cause darkened skin and/or dark spots. It has been known that UV rays irradiation is the primary cause for the activation of the aforesaid skin aging-related mechanisms. Therefore, if UV rays which irradiate the epidermis can be blocked from penetrating into the dermis, or the content or activity of the MMPs in the dermis can be inhibited (such as inhibiting the phosphorylation of MAPK pathway), or melanogenesis can be inhibited, skin aging can be alleviated and the appearance of skin can be improved.

The inventors of the present invention have found that the following caffeamide derivative of formula (I), and/or a pharmaceutically acceptable salt of the caffeamide derivative have the effects of anti-oxidation (such as inhibiting the formation of reactive oxygen species), inhibiting the activity of MMPs, and/or inhibiting the expression of MMPs, and thus, can be used to prevent or alleviate the destruction of collagen:

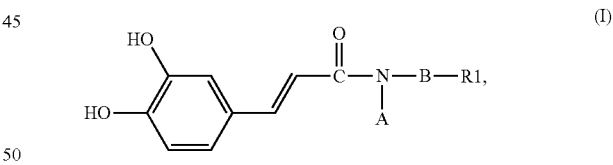

wherein A is H or an alkyl; B is —[CH$_2$]$_m$—; m is an integer ranging from 0 to 10; R1 is H, an optionally substituted phenyl, an optionally substituted pyridyl, —OH, or —OCH$_3$; or N, A, B, and R$_1$ together form an optionally substituted pyrrolyl or piperidyl.

Preferably, in the caffeamide derivative of formula (I), A is H or a C1 to C6 linear alkyl; B is —[CH$_2$]$_m$—; m is an integer ranging from 0 to 8; and R1 is a phenyl optionally substituted by one or two substituents selected from the group consisting of halogen, C1 to C10 alkyl, C1 to C10 alkoxy, —OH, and —NO$_2$. R1 is more preferred to be a phenyl optionally substituted by one or two substituents selected from the group consisting of F, Br, —OCH$_3$, —OH, and —NO$_2$.

In some embodiments of the present invention, the active component is preferably selected from the group consisting of the following compounds:

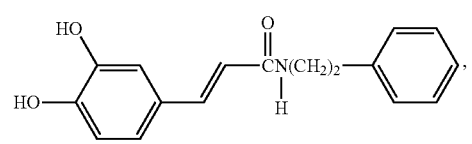 (1)
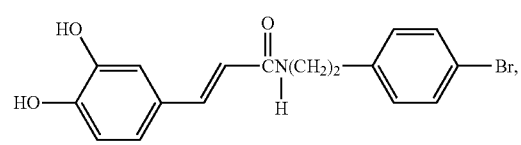 (2)
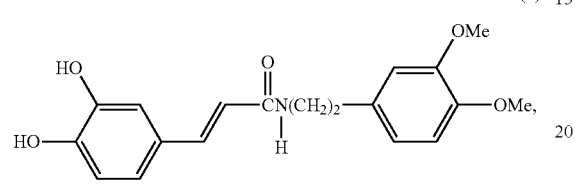 (3)
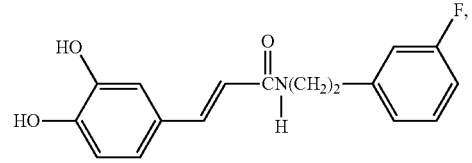 (4)
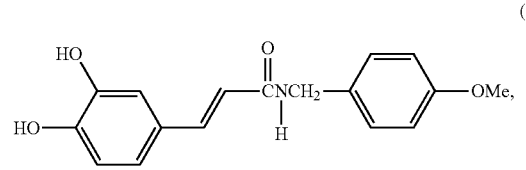 (5)
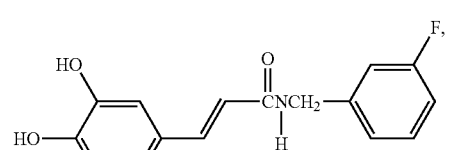 (6)
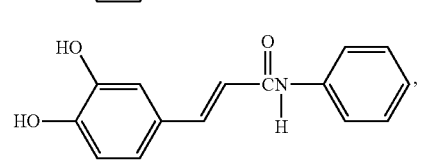 (7)
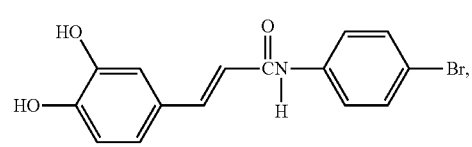 (8)
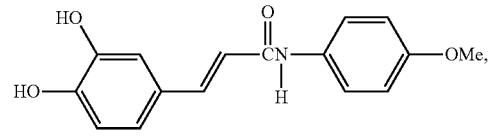 (9)
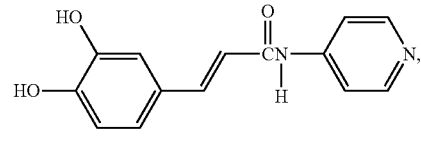 (10)
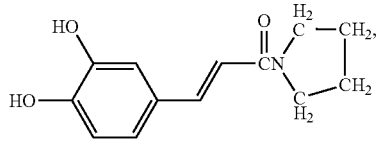 (11)
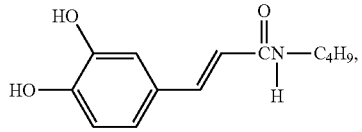 (12)
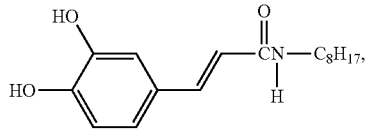 (13)
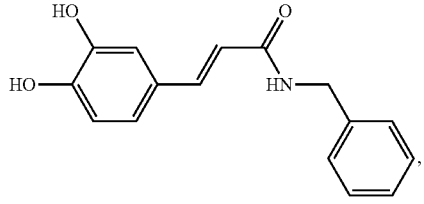 (14)
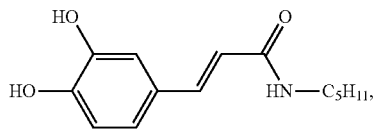 (15)
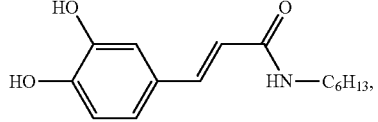 (16)
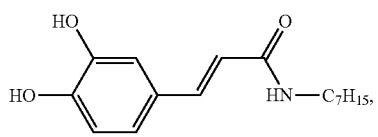 (17)
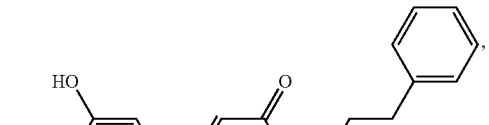 (18)
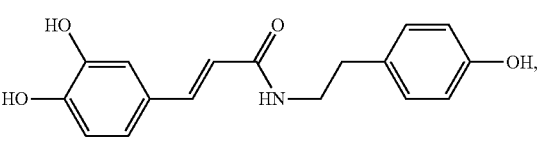 (19)
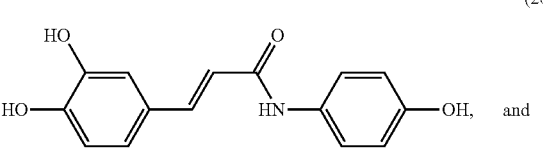 and (20)

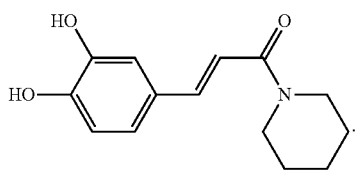

(21)

MMPs can be classified into the following categories: collagenases, stromelysins, gelatinases, matrilysins, and transmembrane type-MMPs. Common MMPs include matrix metalloproteinase-1 (MMP-1), matrix metalloproteinase-2 (MMP-2), matrix metalloproteinase-3 (MMP-3), matrix metalloproteinase-7 (MMP-7), matrix metalloproteinase-8 (MMP-8), matrix metalloproteinase-9 (MMP-9), matrix metalloproteinase-10 (MMP-10), matrix metalloproteinase-11 (MMP-11), matrix metalloproteinase-12 (MMP-12), matrix metalloproteinase-13 (MMP-13), and matrix metalloproteinase-14 (MMP-14). In particular, the caffeamide derivatives and/or their pharmaceutically acceptable salts described herein can effectively inhibit the activity and/or expression of MMP-1, MMP-3 and/or MMP-9.

As described above, the phosphorylation of MAPKs may increase the content of MMPs in the dermis, thereby, further increasing the decomposition of collagen and reducing the content of collagen in the skin. As a result, the skin darkens and even wrinkles form. In addition to the effects of inhibiting the activity and/or expression of MMPs, the caffeamide derivatives and their pharmaceutically acceptable salts described herein are effective in inhibiting the phosphorylation of MAPK, and especially in inhibiting the phosphorylation of c-Jun N-terminal Kinase (JNK), extracellular signal-regulated protein kinase (ERK), and p38 protein, and thus, can prevent the destruction of collagen.

In addition, the caffeamide derivatives and/or their pharmaceutically acceptable salts described herein further have the effects of inhibiting the activity and/or expression of tyrosinase, and/or inhibiting the expression of tyrosinase related protein-1 and/or tyrosinase related protein-2. Tyrosinases, tyrosinase related protein-1, and tyrosinase related protein-2 are proteins involved in the melanogenesis in melanocytes. Because the caffeamide derivatives and/or their pharmaceutically acceptable salts described herein can inhibit the activity and/or expression of the aforementioned proteins, they can provide an effect of inhibiting the formation of melanin.

In addition to achieving the effect of anti-skin aging by inhibiting the decomposition of collagen and inhibiting melanogenesis as described above, the caffeamide derivatives and/or their pharmaceutically acceptable salts described herein can absorb UV rays with a wavelength ranging from 210 nm to 400 nm, especially with a wavelength ranging from 280 nm to 335 nm (i.e. UVA and UVB). Therefore, the caffeamide derivatives and/or their pharmaceutically acceptable salts can be used to block UV rays, decrease the amount of UV rays penetrating into the dermis of skin, thereby, decreasing the damage of skin caused by UV rays.

Because the caffeamide derivatives and/or their pharmaceutically acceptable salts described herein can simultaneously provide the effects of (1) anti-oxidation; (2) directly inhibiting the activity and/or expression of MMPs; (3) inhibiting the expression of MMPs by inhibiting the phosphorylation of MAPK; (4) inhibiting melanogenesis; and (5) absorbing UV rays with a wavelength ranging from 210 nm to 400 nm, they can decrease the decomposition or denaturation of collagen and inhibit the formation of melanin, thereby, effectively improving, caring and/or repairing the skin. For example, the caffeamide derivatives and/or their pharmaceutically acceptable salts of the present invention can be used for anti-skin aging (e.g., anti-skin photo-aging), especially in whitening and caring for the skin, such as reducing skin wrinkling, improving skin quality and skin flaccidity, and reducing skin darkness and dark spots.

The caffeamide derivative of formula (I) described herein can be provided by a condensation reaction of caffeic acid and a corresponding amine. For example, a caffeamide derivative described herein can be synthesized by the following steps. First, a proper amount of caffeic acid, dimethyl formamide (DMF), triethylamine ($Et_3N$), and a corresponding amine are mixed. Then, the mixture is placed in an ice bath, mixed with a BOP-containing $CH_2Cl_2$ solution for 30 minutes, and then incubated with stirring at room temperature for 12 hours. The $CH_2Cl_2$ and DMF in the samples are then extracted. Then, partition extraction is performed with water and AcOEt. The crude product is further treated with column chromatography. Finally, the product is recrystallized and purified with AcOEt to provide the caffeamide derivative.

In the aforesaid synthesis procedure, the amine is selected according to the desired caffeamide derivative, based on the variations of the substituents on the structure of the caffeamide derivative. For example, in some embodiments according to the present invention, the following amines are used to synthesize the caffeamide derivatives of formula (1) to formula (21) described herein: phenethylamine, 4-bromophenethylamine, 3,4-dimethoxyphenethylamine, 3-fluorophenethylamin, 4-methoxybenzylamine, 3-fluorobenzylamine, phenylamine, 4-bromophenylamine, 4-methoxyphenylamine, pyridin-4-yl-amine, pyrrolidin-1-yl-amine, butylamine, octylamine, benzylamine, pentylamine, hexylamine, heptylamine, 3-phenylpropylamine, 4-hydroxyphenethylamine, 4-hydroxyphenylamine, and piperidin-1-yl-amine.

The caffeamide derivative of formula (I) is effective in inhibiting the decomposition of collagen and inhibiting melanogenesis, and thus, it can be used for anti-skin aging. Accordingly, the present invention provides a use of a coffeamide derivative of formula (I) and/or a pharmaceutically acceptable salt of the caffeamide derivative in the manufacture of a medicament for anti-skin aging. The substituents and preferable embodiments of the caffeamide derivatives are as described above.

In the present invention, examples of a pharmaceutically acceptable salt of the caffeamide derivative of formula (I) include but are not limited to alkali metal salts, such as sodium salts and potassium salts; alkaline earth metal salts, such as calcium salts, magnesium salts, and barium salts; transition metal salts, such as zinc salts, copper salts, ferric salts, cobalt salts, titanium salts, vanadium salts; aluminium salts; stannum salts; alkanolamine salts, such as diethanolamine salts, 2-amino-2-ethyl-1,3-propanediol salts, and triethanolamine salts; heterocyclic amine salts, such as morpholine salts, piperazine salts, and piperidine salts; and alkali amine salts, such as amine salts, arginine salts, lysine salts and histidine salts.

The medicament manufactured with the use of the coffeamide derivative of formula (I) and/or its pharmaceutically acceptable salt can be used for anti-skin aging, especially for anti-skin photo-aging. In particular, it can be used for preventing the decomposition or denaturation of collagen in the skin (especially Type I collagen) and inhibiting melanogenesis by anti-oxidation, inhibiting the activity and/or expression of MMPs, inhibiting the phosphorylation of MAPK, promoting the expression of collagen, inhibiting the activity and/or expression of tyrosinase, inhibiting the expression of tyrosinase related protein-1 and/or tyrosinase related protein-2, and/or absorbing UV rays with a wavelength ranging from 210 nm to 400 nm. For example, a medicament manufactured with the use of the coffeamide derivative of formula (I) and/or its pharmaceutically acceptable salt can be used for curing and/or delaying the skin aging-related diseases caused by UV rays irradiation, such as skin flaccidity, skin wrinkles, skin darkness, freckles, black spots, age-spots.

Depending on the desired use, the medicament manufactured with the use of the coffeamide derivative of formula (I) and/or its pharmaceutically acceptable salt can be of any suitable form without particular limits. For example, the medicament can be in a form of emulsion, cream, or gel for external use. Furthermore, the medicament can be in a common pharmaceutical form, such as a tablet, capsule, granule, powder, fluid extract, solution, syrup, suspension, emulsion, tincture, intravenous injection, powder injection, suspension injection, powder-suspension injection.

According to the present invention, the dosage of the medicament manufactured with the use of the coffeamide derivative of formula (I) and/or its pharmaceutically acceptable salt may be adjusted according to the age of the treated subject and the purpose of the application (such as reducing skin wrinkles or reducing skin spots), and the usage frequency may also be optionally adjusted. Depending on the final form of the medicament, the medicament may comprise other additives. For instance, when the medicament is prepared as a skin care product for external use, any suitable and appropriate amount of emulsifier, perfume, and other components active in improving skin quality may be added therein. In general, any additives can be added in the medicament, as long as it has no adverse influence on the effects of the caffeamide derivative of formula (I).

In addition, the present invention relates to a use of the coffeamide derivative of formula (I) and/or its pharmaceutically acceptable salt in the manufacture of a skin care product, wherein the substituents of the coffeamide derivative of formula (I) and the preferable embodiments are as described above. The skin care product can be used for improving, caring and/or repairing the skin, anti-skin aging, especially for anti-skin photo-aging, reducing skin wrinkling, tightening skin, anti-sunburn, skin whitening, reducing skin darkness and dark spots.

According to the present invention, the skin care product manufactured by the coffeamide derivative of formula (I) and/or its pharmaceutically acceptable salt can be of any suitable form without particular limits. For example, the skin care product can be in a form of emulsion, cream, gel, sunscreen cream, or sunscreen spray for external use. Alternatively, the skin care product can be prepared in a form of food or drink, such as health foods or beauty drinks.

According to the present invention, the dosage of the skin care product may be adjusted depending on the age of the subject and the purpose of the application (such as tightening skin or whitening skin), and the usage frequency may also be optionally adjusted. Other components and their amounts to be included in the skin care product are dependent on the final form of the product. For instance, when the skin care product is prepared, any suitable and appropriate amount of emulsifier, perfume, and other components (such as arbutin) active in whitening skin may be added therein.

Furthermore, the present invention relates to a method for anti-skin aging in a subject, comprising administering to the subject an effective amount of an active component selected from the group consisting of a caffeamide derivative of formula (I), a pharmaceutically acceptable salt of the caffeamide derivative, and a combination thereof. The substituents and preferable embodiments of the caffeamide derivative of formula (I) are described as above.

The present invention will be further illustrated in detail with specific examples as follows. However, the following examples are provided only for illustrating the present invention, and the scope of the present invention is not limited thereby.

EXAMPLES

Example 1

Preparation of Caffeamide Derivatives

As shown in Table 1, a corresponding amine compound was chosen depending on the desired caffeamide derivative to carry out the relevant procedure. Caffeic acid (100 mg) was dissolved in a reaction bottle which containing 1 ml dimethyl formamide (DMF), 1 ml triethylamine ($Et_3N$), and 1.2 N amine compound. Then, the sample in a beaker was placed in an ice bath at 0° C. 5 ml of BOP-containing $CH_2Cl_2$ solution was added to the beaker. The mixture was stirred for 30 minutes, removed from the ice bath and stirred at room temperature for 12 hours. The $CH_2Cl_2$ and DMF in the sample were then excluded by extraction. Then, partition extraction was performed with water and AcOEt, and an AcOEt layer was obtained. The AcOEt layer was sequentially washed with 3 N HCl solution and 10% $Na_2CO_3$ solution, and unnecessary water was removed by $MgSO_4$. The AcOEt was excluded by extraction. Then, the crude product was further analyzed by column chromatography, eluted and purified by a mixture solution of $CH_2Cl_2$ and AcOEt with a ratio of 1:1. Finally, the products were recrystallized and purified with AcOEt to obtain the caffeamide derivatives. The structures of the caffeamide derivatives (formula (1) to formula (21)) are shown in Table 1.

TABLE 1

| Amine compounds | Caffeamide derivatives | |
| --- | --- | --- |
| phenethylamine | [structure: HO and HO substituted benzene ring connected via CH=CH to C(=O)N(H)(CH₂)₂-phenyl] | Formula (1) |

TABLE 1-continued

| Amine compounds | Caffeamide derivatives | |
|---|---|---|
| 4-bromophenethylamine | (structure: 3,4-dihydroxycinnamoyl-NH-(CH$_2$)$_2$-(4-bromophenyl)) | Formula (2) |
| 3,4-dimethoxyphenethylamine | (structure: 3,4-dihydroxycinnamoyl-NH-(CH$_2$)$_2$-(3,4-dimethoxyphenyl)) | Formula (3) |
| 3-fluorophenethylamine | (structure: 3,4-dihydroxycinnamoyl-NH-(CH$_2$)$_2$-(3-fluorophenyl)) | Formula (4) |
| 4-methoxybenzylamine | (structure: 3,4-dihydroxycinnamoyl-NH-CH$_2$-(4-methoxyphenyl)) | Formula (5) |
| 3-fluorobenzylamine | (structure: 3,4-dihydroxycinnamoyl-NH-CH$_2$-(3-fluorophenyl)) | Formula (6) |
| phenylamine | (structure: 3,4-dihydroxycinnamoyl-NH-phenyl) | Formula (7) |
| 4-bromophenylamine | (structure: 3,4-dihydroxycinnamoyl-NH-(4-bromophenyl)) | Formula (8) |
| 4-methoxyphenylamine | (structure: 3,4-dihydroxycinnamoyl-NH-(4-methoxyphenyl)) | Formula (9) |
| pyridin-4-yl-amine | (structure: 3,4-dihydroxycinnamoyl-NH-(pyridin-4-yl)) | Formula (10) |
| pyrrolidin-1-yl-amine | (structure: 3,4-dihydroxycinnamoyl-N(pyrrolidin-1-yl)) | Formula (11) |

TABLE 1-continued

| Amine compounds | Caffeamide derivatives | |
|---|---|---|
| butylamine | 3,4-dihydroxyphenyl-CH=CH-C(=O)-NH-C₄H₉ | Formula (12) |
| octylamine | 3,4-dihydroxyphenyl-CH=CH-C(=O)-NH-C₈H₁₇ | Formula (13) |
| benzylamine | 3,4-dihydroxyphenyl-CH=CH-C(=O)-NH-CH₂-C₆H₅ | Formula (14) |
| pentylamine | 3,4-dihydroxyphenyl-CH=CH-C(=O)-NH-C₅H₁₁ | Formula (15) |
| hexylamine | 3,4-dihydroxyphenyl-CH=CH-C(=O)-NH-C₆H₁₃ | Formula (16) |
| heptylamine | 3,4-dihydroxyphenyl-CH=CH-C(=O)-NH-C₇H₁₅ | Formula (17) |
| 3-phenylpropylamine | 3,4-dihydroxyphenyl-CH=CH-C(=O)-NH-(CH₂)₃-C₆H₅ | Formula (18) |
| 4-hydroxyphenethylamine | 3,4-dihydroxyphenyl-CH=CH-C(=O)-NH-CH₂CH₂-C₆H₄-OH | Formula (19) |
| 4-hydroxyphenylamine | 3,4-dihydroxyphenyl-CH=CH-C(=O)-NH-C₆H₄-OH | Formula (20) |
| piperidin-1-yl-amine | 3,4-dihydroxyphenyl-CH=CH-C(=O)-N(piperidinyl) | Formula (21) |

Example 2

Anti-Oxidation Test (1) Scavenging Test of DPPH Free Radical

DPPH (1,1-diphenyl-2-picrylhydrazyl) was used as a source of free radicals to examine the scavenging efficiency of the caffeamide derivatives prepared in Example 1 on free radicals. Different concentrations (1 μM to 50 μM) of 100 μl compound of formula (1) or formula (2) were added into a 96-well microplate, and well mixed with 100 μl of 200 μM DPPH solution (dissolved in water). The mixtures were placed in the dark at room temperature for 30 minutes and its absorbance at 517 nm was measured by an enzyme immunoassay analyzer. In this experiment, 50 volume % propanediol was used to replace extracts and to be a control group, ascorbic acid (vitamin C) was used as a positive control group, and methanol was used to replace DPPH as the background value. The scavenging efficiency of caffeamide derivatives on free radicals was examined by the formula blow, and the results are shown in Table 2, FIG. 1a, and FIG. 1b.

Scavenging efficiency(%)=[the absorbance of the control group−the absorbance of the experimental group/the absorbance of the control group]×100%.

TABLE 2

| Sample | Concentration (μM) | Scavenging efficiency (%) |
| --- | --- | --- |
| Ascorbic acid | 25 | 57.5 ± 1.4 |
|  | 50 | 89.8 ± 0.9 |
| Compound of formula (1) | 1 | 11.7 ± 5.5 |
|  | 5 | 20.9 ± 2.6 |
|  | 10 | 27.1 ± 4.3 |
|  | 25 | 59.1 ± 2.7 |
|  | 50 | 96.8 ± 1.4 |
| Compound of formula (2) | 1 | 6.4 ± 4.9 |
|  | 5 | 12.9 ± 3.5 |
|  | 10 | 26.5 ± 0.9 |
|  | 25 | 62.1 ± 2.9 |
|  | 50 | 96.6 ± 0.4 |

The results in Table 2, FIG. 1a and FIG. 1b show that the compound of formula (1) can scavenge DPPH free radical in a concentration dependent way. The scavenging efficiency of the compound of formula (1) is similar to that of ascorbic acid when their concentration are 25 μM and better than that of ascorbic acid when their concentration are 50 μM. The $SC_{50}$ of the compound of formula (1) is 22.1±1.3 μM. The compound of formula (2) also has a concentration dependency and a better scavenging efficiency than that of ascorbic acid when it is in a concentration of 25 μM or 50 μM. The $SC_{50}$ of the compound of formula (2) is 20.0±1.0 μM.

(2) Scavenging Test of ROS Free Radicals

First, human fibroblast Hs68 cells were irradiated with UVB with an intensity of 80 mJ/cm² for 30 seconds to increase 1.3 times of intracellular ROS level. Then, human fibroblast Hs68 cells in a 96-well microplate (with a density of 1×10⁴ per well) were added with different concentrations (0 μM to 25 μM) of compounds of formula (1) or formula (2) prepared in Example 1. After incubated in an incubator (37° C., 5% $CO_2$) for 24 hours, the ROS level was examined. The results are shown in Table 3, FIG. 2a and FIG. 2b.

TABLE 3

|  | 0 | 0 | 5 | 10 | 25 |
| --- | --- | --- | --- | --- | --- |
| Compound of formula (1) (μM) |  |  |  |  |  |
| Concentration of ROS (times compared to the untreated cells) | 1.0 ± 0.05 | 1.3 ± 0.08 | 1.2 ± 0.13 | 1.0 ± 0.21 | 0.8 ± 0.07 |
| Compound of formula (2) (μM) |  |  |  |  |  |
| Concentration of ROS (times compared to the untreated cells) | 1.0 ± 0.01 | 1.3 ± 0.03 | 1.0 ± 0.09 | 0.9 ± 0.02 | 0.8 ± 0.04 |

Figure 2:
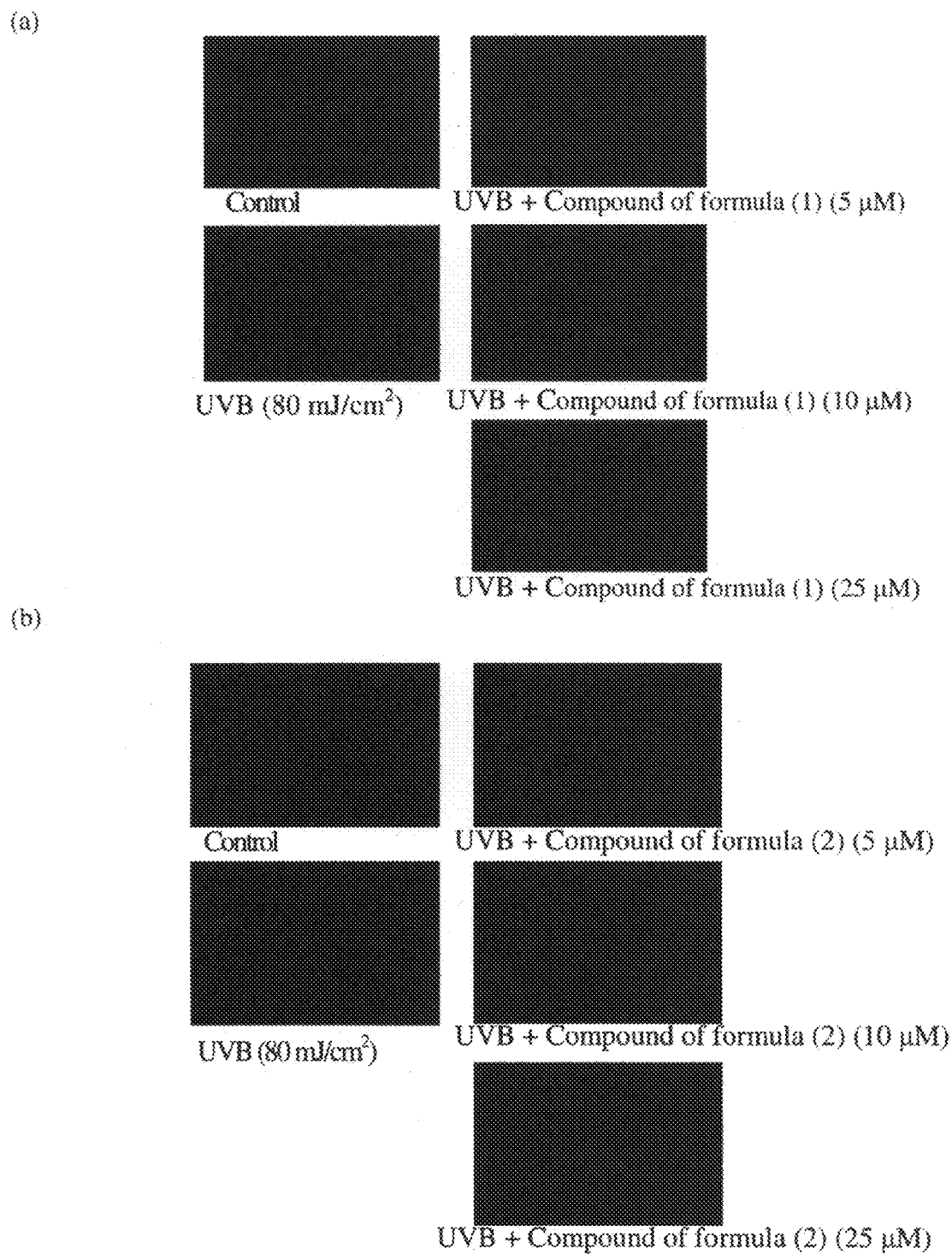
FIGS. 2a and 2b are immunofluorescence staining pictures showing the scavenging efficiency of the caffeamide derivatives of the present invention on ROS free radicals.

The results in Table 3, FIG. 2a and FIG. 2b show that intracellular ROS level can be scavenged by treating the cells with the compound of formula (1) in a concentration dependent way. The intracellular ROS level was similar to that of the group untreated with caffeamide derivative when the concentration of compound of formula (1) was 10 μM and was 0.8 times over that of the group untreated with caffeamide derivative when the concentration of compound of formula (1) was 25 μM. After the cells were treated with compound of formula (2), the intracellular ROS level was similar to that of the un-irradiated group when the concentration of compound of formula (2) was 5 μM and was 0.9 times and 0.8 times over that of the un-irradiated group respectively when the concentration of compound of formula (1) were 10 μM and 25 μM.

Example 3

Inhibition Test of the MMP Activity

Human fibroblast Hs68 cells (5×10⁵) (the number of Bioresource Collection and Research Center (BCRC): 60038) were counted and incubated in a culture dish with a diameter of 10 cm (the culture dish components were adjusted by L-glutamine (4 mM) to have 1.5 g/L $NaHCO_3$, 4.5 g/L glucose, and 90% Dulbecco's Modified Eagle's Medium with 10% fetal bovine serum (FBS)). The medium was removed until human fibroblast Hs68 cells grow to a confluence of 80%, and the cells were then washed once with 5 ml PBS (phosphate buffered saline). Then, 3 ml phenol red-free medium which contain different concentrations (0 μM to 25 μM) of the compounds of formula (1) or formula (2) prepared in Example 1 were added into the culture dish. After incubating for 1 hour, the cells were irradiated by UV light (UVB with an intensity of 40 mJ/cm²) for 15 seconds. Next, the phenol red-free medium which contains different concentrations (0 μM to 25 μM) of the compounds of formula (1) or formula (2) prepared in Example 1 were added into the culture dish sequentially. After incubation in an incubator (37° C., 5% $CO_2$) for 48 hours, the cells were collected.

The collected cells were treated with a sonication buffer (containing $Na_3VO_4$ (100 μM), phenylmethanesulfonyl fluoride (PMSFL, 100 mg/ml), leupeptin (20 mg/ml), Tris-HCl (pH 7.4, 50 μM), NaCl (37.5 μM), DL-dithiothretiol (250 μM), sodium deoxycholate (3 μM), EDTA (1 μM), SDS (0.1%), and Igepal™ CA-630 (Sigma-Aldrich, 1%)) and sonicated to rupture the cell membranes. Then, the organelles and fragments of the cells were precipitated by centrifugation, and the supernatant, which contains proteins in the cytosol was collected. Next, the obtained proteins were separated by SDS-PAGE, and transferred to a membrane by western blotting. Antibodies were used to recognize the targeted proteins, such as MMP-1, MMP-3, MMP-9, and actin. The images were recorded by a Luminescent imagination technology (LAS-4000, FUJIFILM), and the variation of the proteins expression levels were determined by a quantitative analysis software (multi Gauge 2.2, Steware Technology Inc.).

Figure 3:
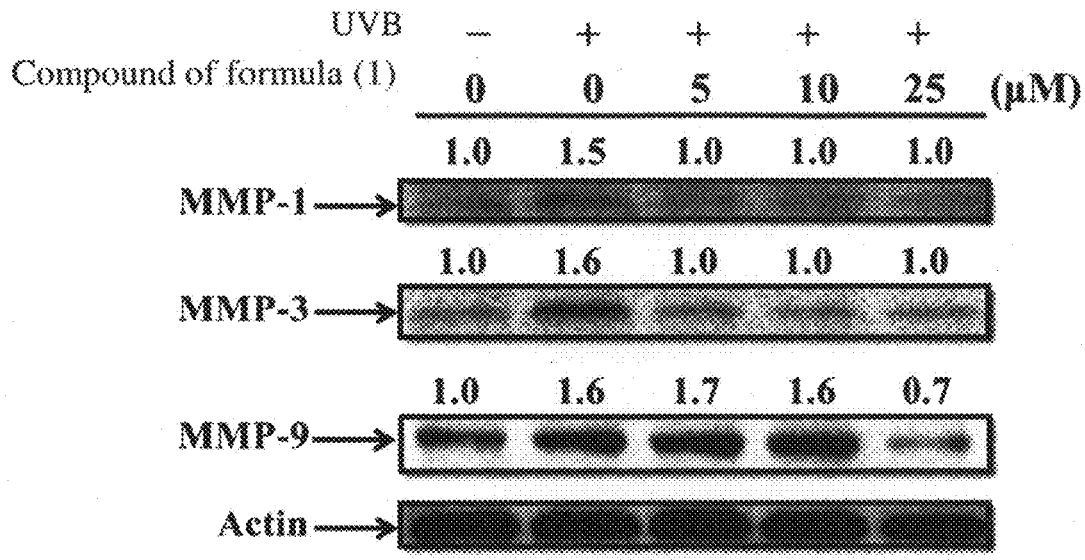
FIGS. 3a and 3b are western blot pictures showing MMP-1, MMP-3 and MMP-9 in human fibroblast Hs68 cells.
Figure 3:
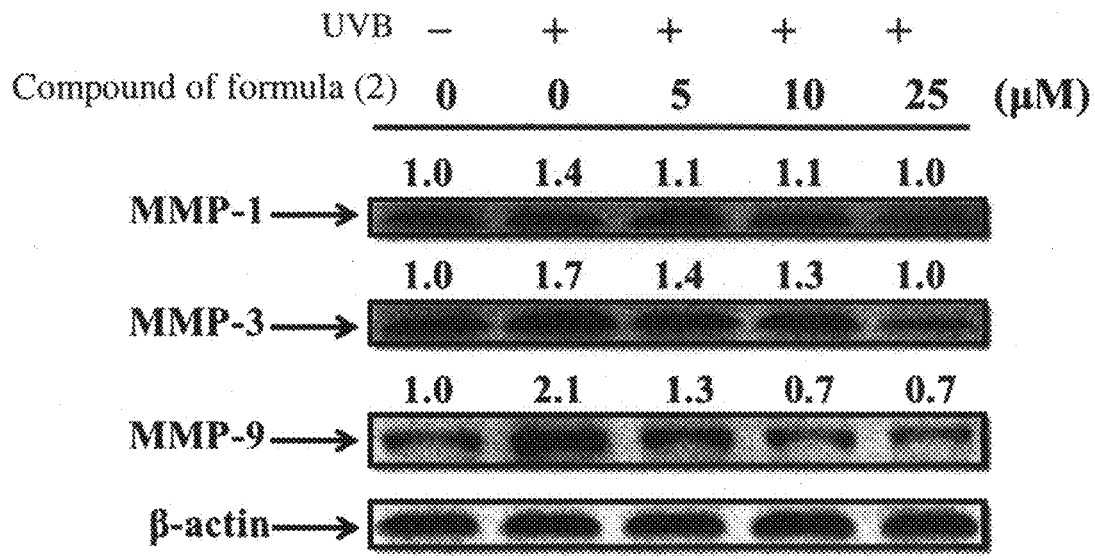

FIG. 3a shows the variation of the content of the MMPs in the cells treated with the compound of formula (1). After irradiation by UV rays, the expression levels of MMP-1, MMP-3 and MMP-9 of human fibroblast cells were increased by 1.5 times, 1.6 times and 1.6 times, respectively. After exposure to UV rays and being treated with the compound of formula (1) prepared in Example 1, the expression levels of the MMPs in the cells induced by UVB were inhibited in a concentration dependent way. Specifically, when the concentration of the compound of formula (1) was 5 µM, the expression level of MMP-1 and MMP-3 was 1.0 time as compared to that of the untreated cells. When the concentration of the compound of formula (1) was 25 µM, the expression level of MMP-9 was 0.7 times as compared to that of the untreated cells.

FIG. 3b shows the variation of the content of MMPs in the cells treated with the compound of formula (2). After irradiation by UV rays, the expression levels of MMP-1, MMP-3 and MMP-9 of human fibroblast Hs68 cells were increased by 1.4 times, 1.7 times and 2.1 times, respectively. After exposure to UV rays and treated with the compound of formula (2) prepared in Example 1, the expression level of the MMPs in the cells induced by UVB were inhibited in a concentration dependent way. Specifically, when the concentration of the compound of formula (2) was 5 µM, the expression level of MMP-1 was 1.1 times as compared to that of the untreated cells. When the concentration of the compound of formula (2) was 25 µM, the expression level of MMP-3 was 1.0 times as compared to that of the untreated cells. And, when the concentration of the compound of formula (2) was 10 µM, the expression level of MMP-9 was 0.7 times as compared to that of the untreated cells.

Example 4

Inhibition Test of the Phosphorylation of MAPK

It has been known that the skin photo-aging caused by UV rays will increase the content of MMPs in the dermis by the phosphorylation of MAPK. In this experiment, the effect of caffeamide derivative on the phosphorylation of MAPK in the cells was analyzed by western blotting. The results are shown in FIG. 4a and FIG. 4b.

Figure 4:
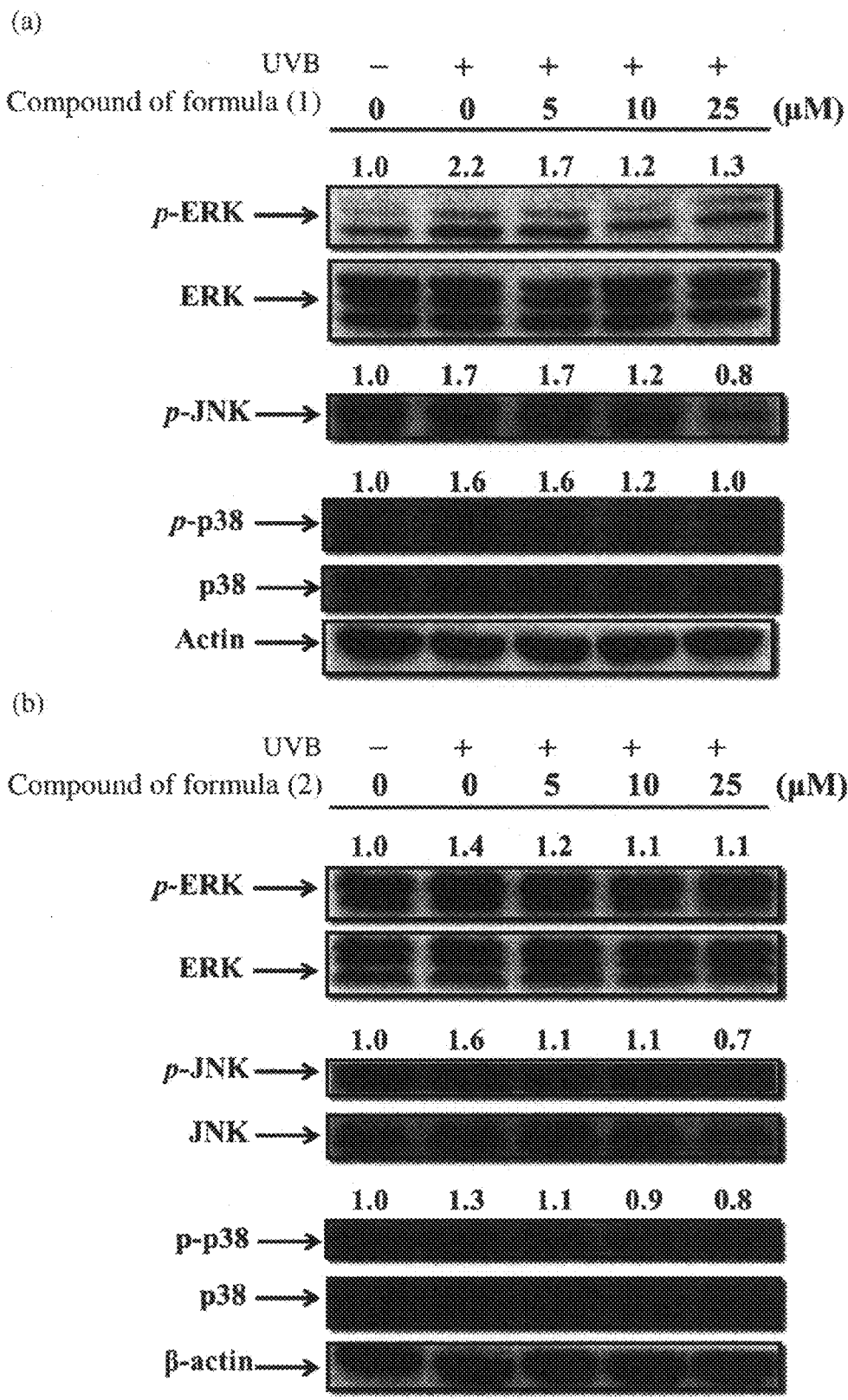
FIGS. 4a and 4b are western blot pictures showing non-phosphorylated and phosphorylated MAPKs (JNK, ERK and p38) in human fibroblast Hs68 cells.

As shown in FIG. 4a, after human fibroblast Hs68 cells were irradiated with UVB with an intensity of 40 mJ/cm$^2$ for 15 seconds, the expression levels of three phosphorylated MAPK (i.e., c-Jun n-terminal kinase (JNK), ERK and p38) were increased by 2.2 times, 1.7 times, and 1.6 times, respectively. However, the expression of the phosphorylated-JNK, ERK and p38 of the cells treated with the compound of formula (1) prepared in Example 1 were inhibited in a concentration dependent way. Specifically, when the concentration of the compound of formula (1) was 10 µM, the expression level of p-ERK, p-JNK and p-p38 was 1.2 times as compared to that of the untreated cells. When the concentration of compound of formula (1) was 25 mM, the expression levels of p-ERK, p-JNK and p-p38 were 1.3 times, 0.8 times, and 1.0 times as compared to those of the untreated cells, respectively.

As shown in FIG. 4b, after human fibroblast Hs68 cells were irradiated with UVB with an intensity of 40 mJ/cm$^2$ for 15 seconds, the expression levels of the phosphorylated JNK, ERK and p38 proteins were increased by 1.4 times, 1.6 times, and 1.3 times, respectively. After being treated with the compound of formula (2) prepared in Example 1, the protein expression levels of the MAPKs induced by UVB were inhibited in a concentration dependent way. Specifically, when the concentration of the compound of formula (2) was 10 µM, the expression level of P-ERK was 1.1 times as compared to that of the untreated cells. When the concentration of the compound of formula (2) was 5 µM, the expression levels of p-JNK and p-p38 were both 1.1 times as compared to that of the untreated cells.

The results of this test suggest that the caffeamide derivatives described herein can inhibit the expression of MMPs by inhibiting MAPK pathway to prevent the decomposition of collagen.

Example 5

Inhibition Test of Activator Protein 1 Gene Transcription Factors

When cells are irradiated by UV rays, JNK, p38 and c-Jun in the cells will translocated into the nucleus, and c-For will translocate into the nucleus under the regulation of ERK and p38. The two subunits of c-Jun and c-Fos will combine to form an AP-1 gene transcription factor to participate in gene expression process and increase the mRNA transcription level of MMP-1. On the other hand, the two subunits can also reduce the gene expression level of procollagen a1 of Type I collagen. Therefore, in this experiment, the expression of AP-1 in the nucleus was analyzed by western blotting. The results are shown in FIG. 5a and FIG. 5b.

Figure 5:
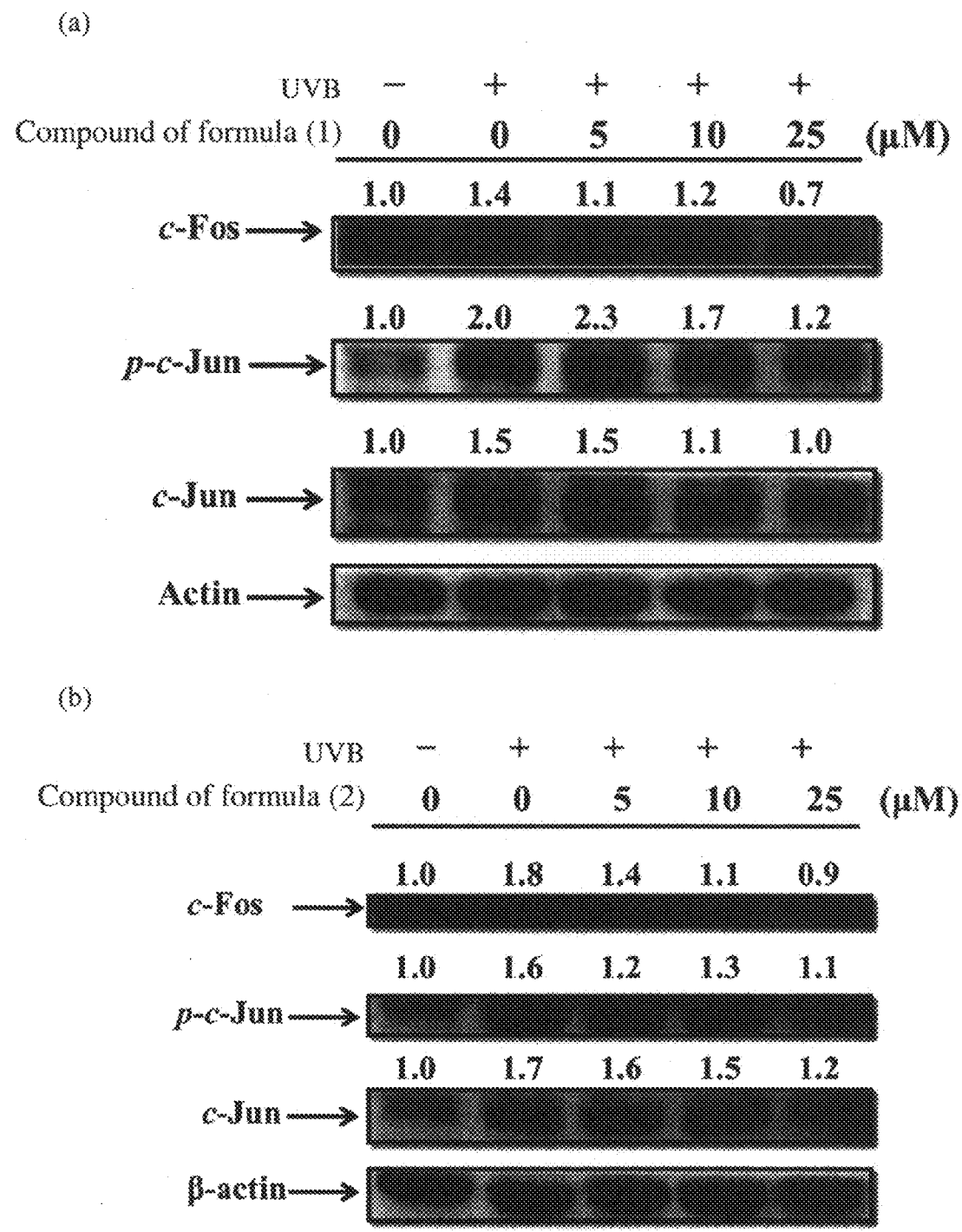
FIGS. 5a and 5b are western blot pictures showing activator protein 1 (AP-1) gene transcription factors (c-Fos, p-c-Jun, and c-Jun) in human fibroblast Hs68 cells.

As shown in FIG. 5a, after human fibroblast Hs68 cells were irradiated with UVB with an intensity of 40 mJ/cm$^2$ for 24 hours, the protein expression levels of c-Fos, p-c-Jun, and c-Jun were increased by 1.4 times, 2.0 times, and 1.5 times, respectively. However, after the cells were treated with the compound of formula (1) prepared in Example 1, the protein expression levels of c-Fos, p-c-Jun, and c-Jun induced by UVB were inhibited in a concentration dependent way. Specifically, when the concentration of the compound of formula (1) was 5 µM, the expression level of c-Fos was 1.1 times as compared to that of the untreated cells. When the concentration of the compound of formula (1) was 25 µM, the expression levels of p-c-Jun was 1.2 times as compared to that of the untreated cells. When the concentration of the compound of formula (1) was 10 µM, the expression level of c-Jun was 1.1 times as compared to that of the untreated cells.

As shown in FIG. 5b, after human fibroblast Hs68 cells were irradiated with UVB with an intensity of 40 mJ/cm$^2$ for 24 hours, the protein expression levels of c-Fos, p-c-Jun, and c-Jun were increased by 1.8 times, 1.6 times, and 1.7 times, respectively. However, after the cells were treated with the compound of formula (2) prepared in Example 1, the protein expression levels of c-Fos, p-c-Jun, and c-Jun induced by UVB were inhibited in a concentration dependent way. Specifically, when the concentration of the compound of formula (2) was 10 µM, the expression level of c-Fos was 1.1 as compared to that of the untreated cells. When the concentration of the compound of formula (1) was 25 µM, the expression levels of p-c-Jun and c-Jun were 1.1 times and 1.2 times, respectively, as compared to that of the untreated cells.

The results of this test suggest that the caffeamide derivatives described herein can affect the translocation of AP-1 into nucleus by inhibiting the phosphorylation of MAPK induced by UV rays to inhibit the gene transcription of MMP-1 and procollagen-Iα1 and prevent the decomposition of collagen.

Example 6

Promotion Test of the Expression of Collagen

It has been known that Smad3 protein can promote the expression level of procollagen-1, and Smad7 protein can inhibit the expression level of Smad3 protein. After cells were irradiated with UV rays, the expression levels of procollagen-1 and Smad3 protein will reduce and the expression level of Smad7 protein will increase. Therefore, in this experiment, the expression levels of intracellular procollagen-1 protein, Smad3 protein and Smad7 protein were analyzed by western blotting. The results are shown in FIG. 6a and FIG. 6b.

Figure 6:
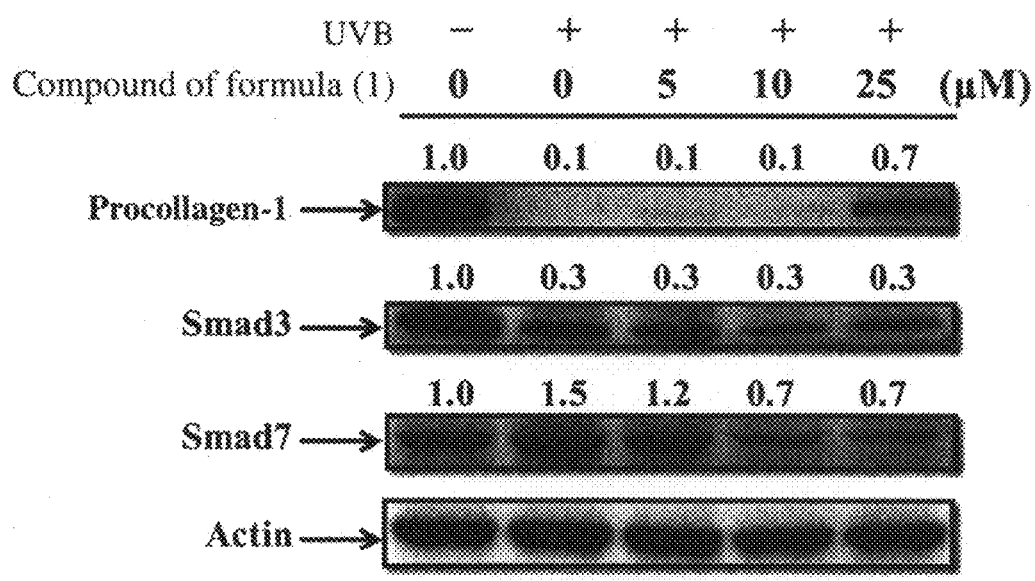
FIGS. 6a and 6b are western blot pictures showing procollagen-1, Smad3 and Smad7 in human fibroblast Hs68 cells.
Figure 6:
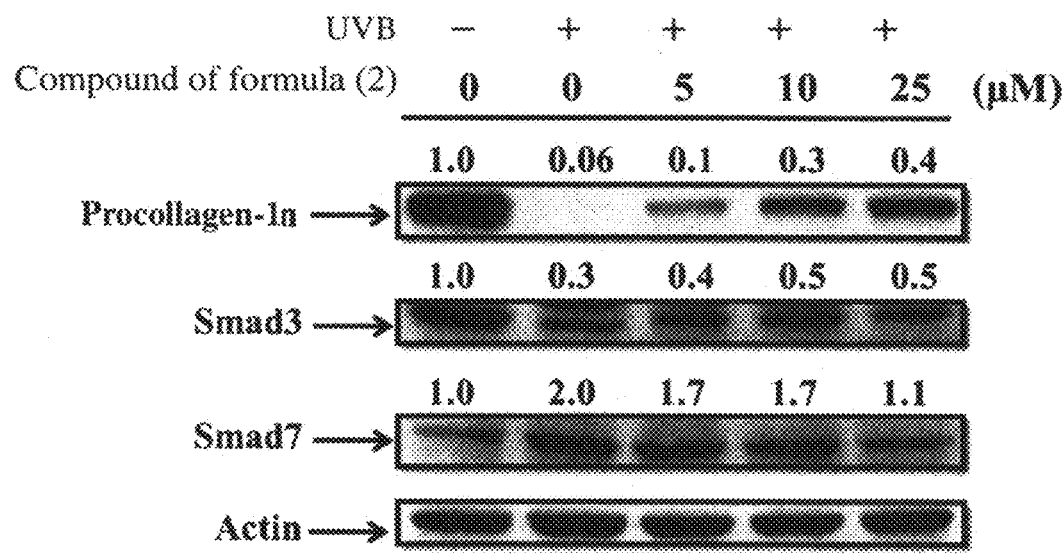
Figure 7:
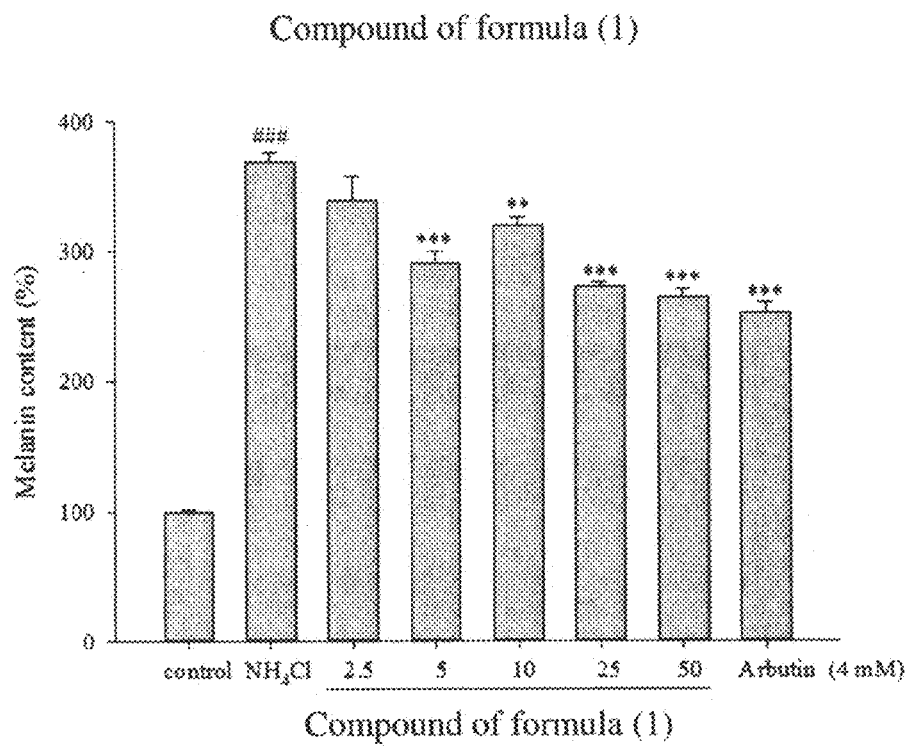
FIGS. 7a to 7k are statistical bar diagrams showing the inhibition of the caffeamide derivatives of the present invention on the expression of melanin in B16 cells.
Figure 7:
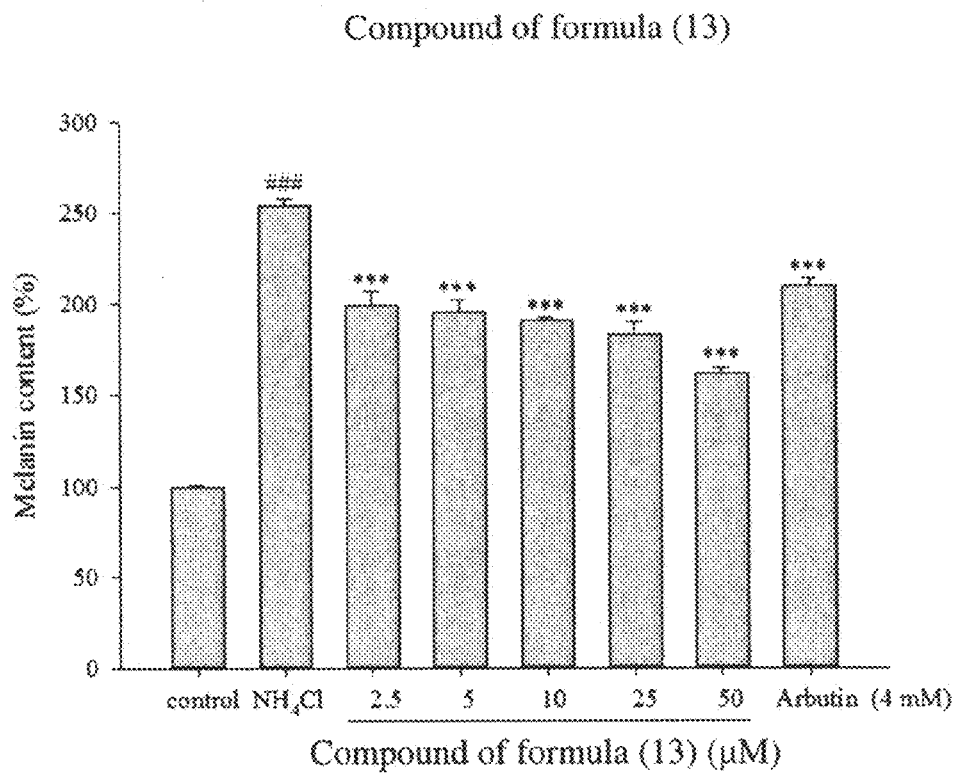
Figure 7:
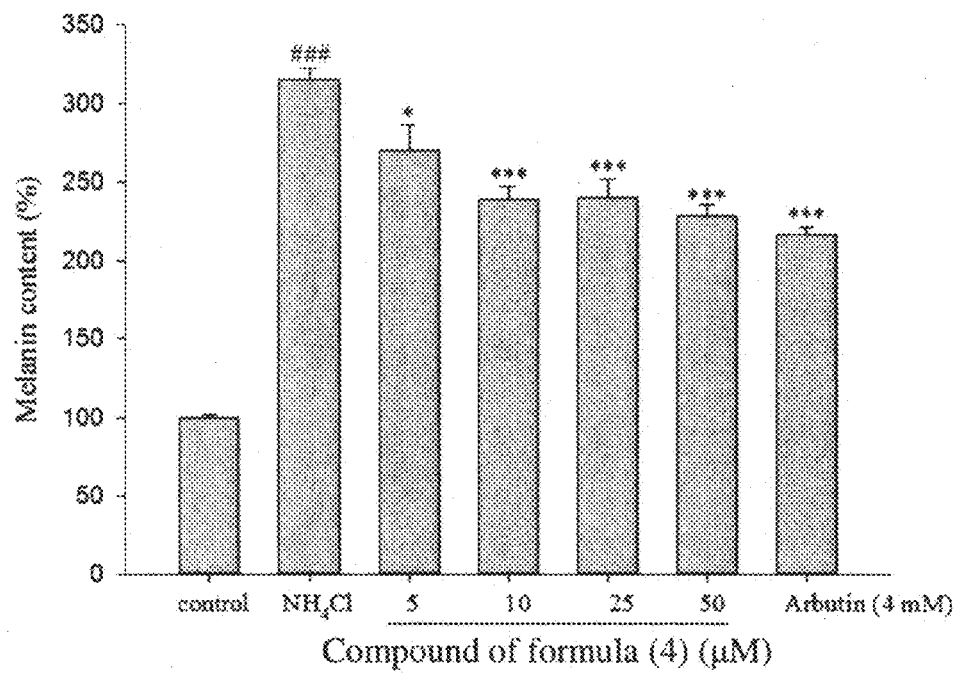
Figure 7:
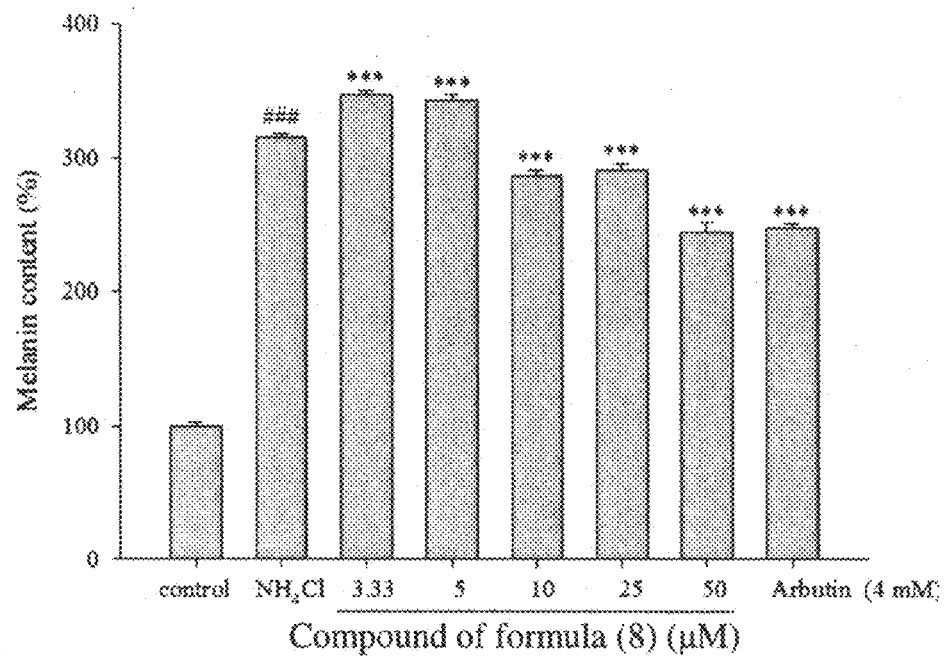
Figure 7:
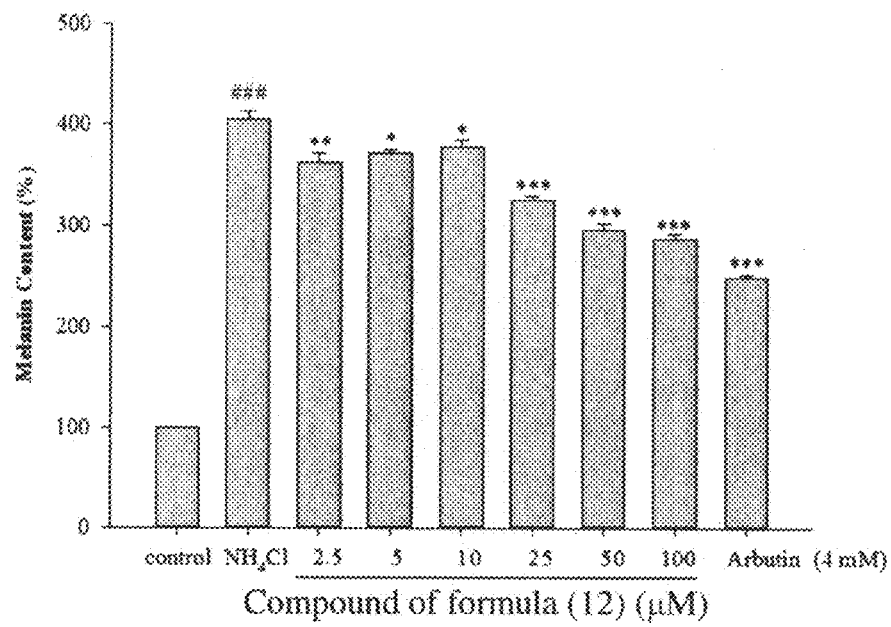
Figure 7:
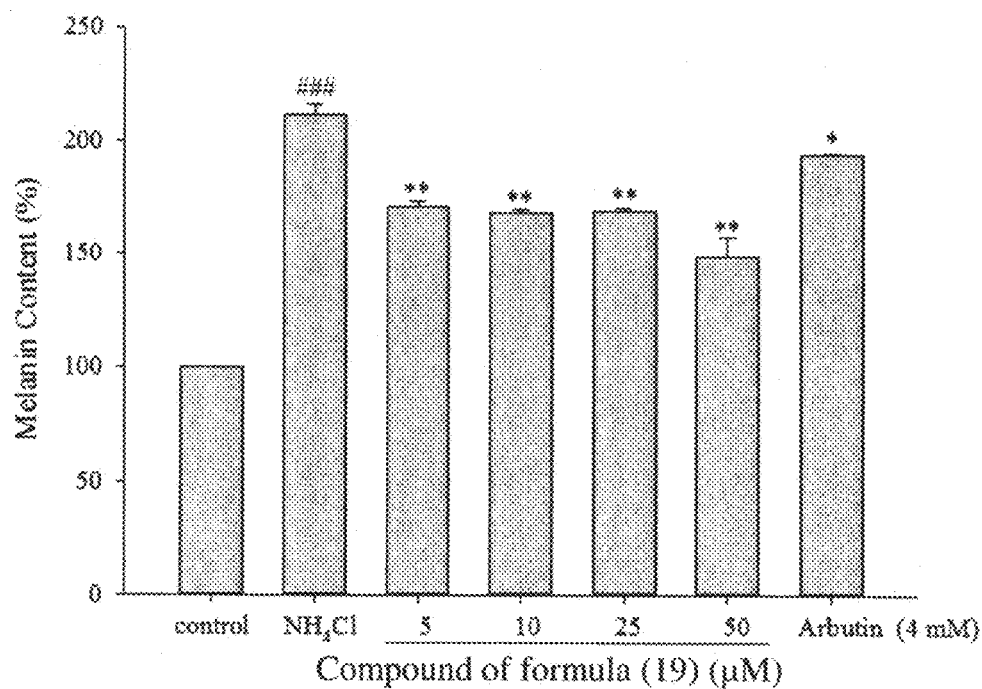
Figure 7:
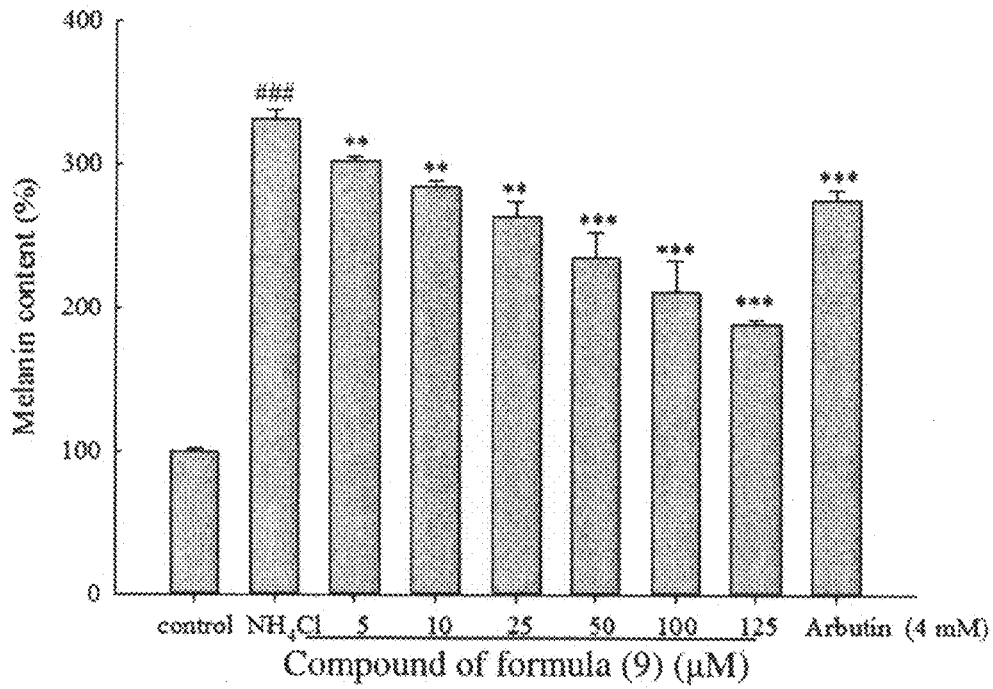
Figure 7:
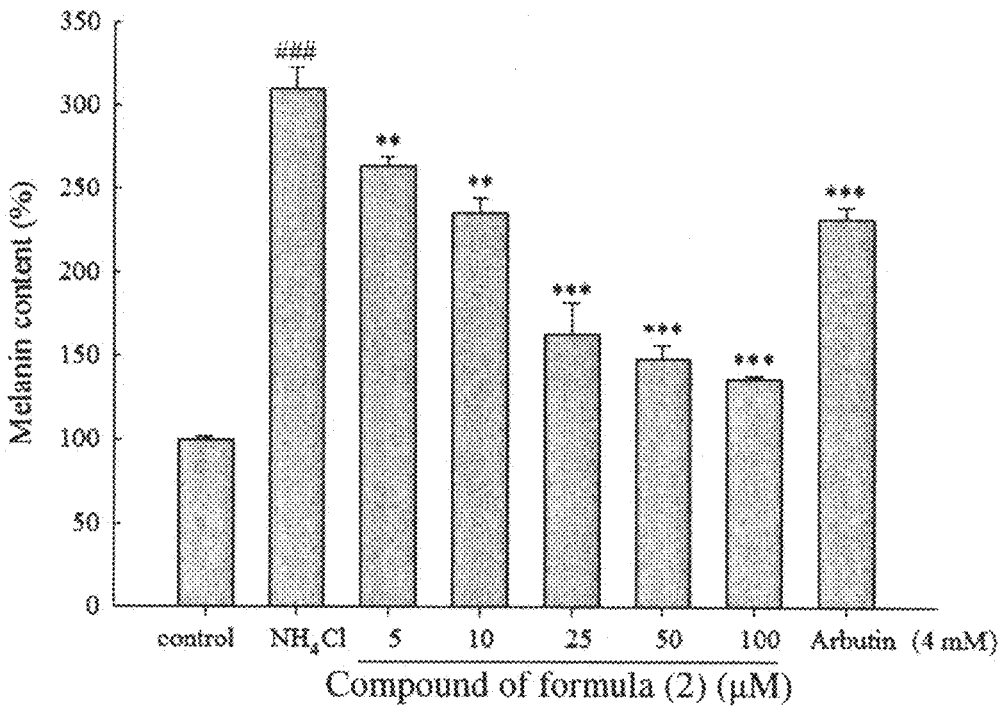
Figure 7:
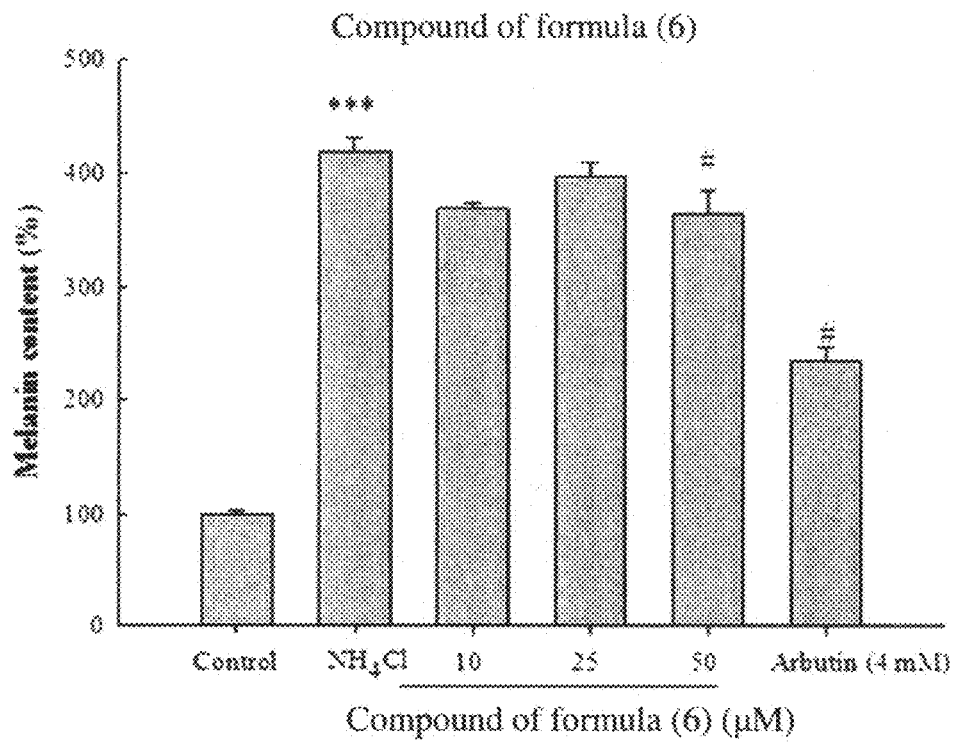
Figure 7:
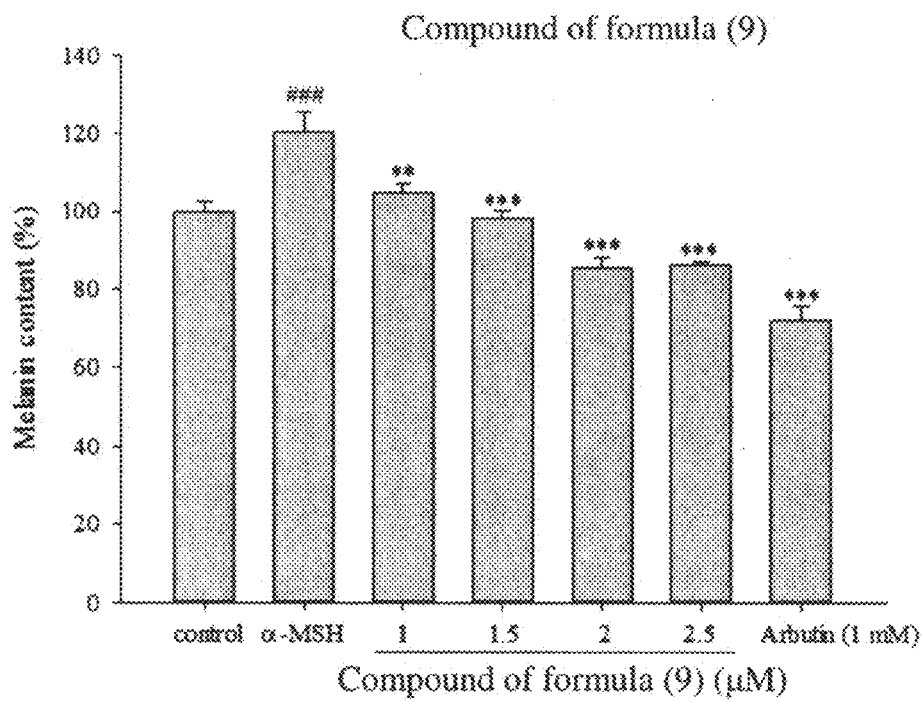
Figure 7:
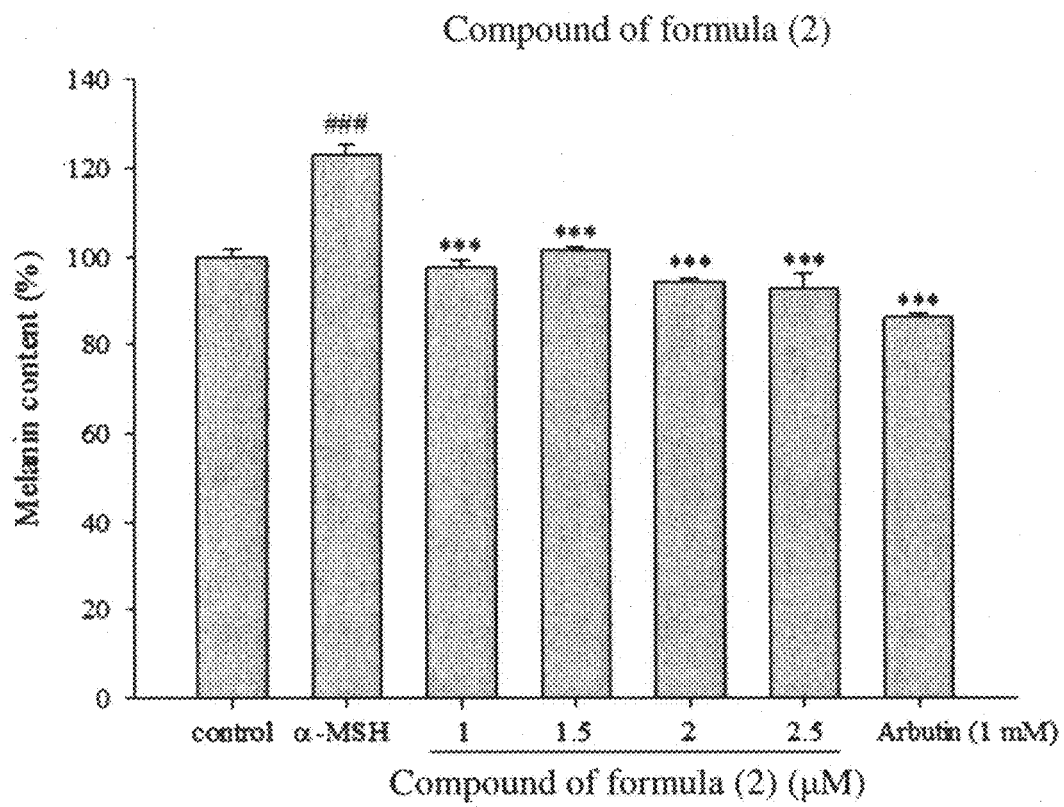

As shown in FIG. 6a, after human fibroblast Hs68 cells were irradiated with UVB with an intensity of 40 mJ/cm$^2$ for 24 hours, the protein expression levels of procollagen-1 and Smad3 in the cells were decreased by 0.1 times and 0.3 times, respectively, and the protein expression level of Smad7 was increased by 1.5 times. However, after the cells were treated with the compound of formula (1) prepared in Example 1, the protein expression level of procollagen-1 decreased by UVB can be reversed to 0.7 times when the concentration of the compound of formula (1) was 25 μM, the protein expression level of Smad3 was not affected, and the protein expression level of Smad7 induced by UVB can be effectively inhibited in a concentration dependent way. Specifically, when the concentration of the compound of formula (1) was 5 μM, the protein expression level of Smad7 was 1.2 times as compared to that of the untreated cells. When the concentration of the compound of formula (1) was 10 μM or 25 μM, the protein expression level of Smad7 was 0.7 times as compared to that of the untreated cells.

As shown in FIG. 6b, after human fibroblast Hs68 cells were irradiated with UVB with an intensity of 40 mJ/cm$^2$ for 24 hours, the protein expression levels of procollagen-1 and Smad3 in the cells were decreased by 0.06 times and 0.3 times, respectively, and the protein expression level of Smad7 was increased by 2.0 times. However, after the cells were treated with the compound of formula (2) prepared in Example 1, the protein expression levels of procollagen-1 and Smad3 inhibited by UVB can be reversed to 0.4 times and 0.5 times, respectively, when the concentration of the compound of formula (1) was 25 μM, and the protein expression level of Smad7 induced by UVB can be effectively inhibited in a concentration dependent way. Specifically, when the concentration of the compound of formula (2) was 25 μM, the protein expression level of Smad7 was 1.1 times as compared to that of the untreated cells.

This test suggests that the caffeamide derivatives described herein can inhibit the expression level of Smad7 protein by increasing the protein expression level of procollagen-1 and Smad3 to increase the content of collagen.

Example 7

Inhibition Test of Melanin Formation (1) Content Analysis of Melanin

Mouse melanoma B16 cells were stimulated by 5 N NH$_4$Cl or 0.5 μM α-MSH (for a NH$_4$Cl treated group, 2×10$^5$ cells were treated for 24 hours; for a α-MSH group, 7×10$^4$ cells were treated for 48 hours) to induce the formation of melanin. Then, B16 cells stimulated by NH$_4$Cl or α-MSH were treated with different concentrations (1 μM to 50 μM) of caffeamide derivatives of formula (1), (2), (4), (6), (8), (9), (12), (13), or (19) prepared in Example 1, respectively, to inhibit the formation of melanin. Next, the content of melanin in the cells was analyzed by western blotting. Arbutin was used as a positive control in this experiment. The results are shown in FIGS. 7a to 7k.

FIGS. 7a to 7i show the content of the melanin of B16 cells stimulated by NH$_4$Cl and treated by the compounds of formula (1), (13), (4), (8), (12), (19), (9), (2), or (6) of the present invention. FIGS. 7j to 7k show the content of melanin of the B16 cells stimulated by α-MSH and treated by the compounds of formula (9) or (2) of the present invention. According to the results in FIGS. 7a to 7k, it can be known that the caffeamide derivatives described herein can effectively inhibit the expression of melanin of the cells and has an effect of skin whitening.

(2) Activity Analysis of Tyrosinase

It has been known that tyrosinase is one of the primary protein participating in melanogenesis. In this experiment, different concentrations (5 μM to 125 μM) of the compounds of formula (9) or (2) prepared in Example 1 were used to treat B16 cells (1.5×10$^4$) for 48 hours, and the activity of tyrosinase was analyzed by western blotting.

Figure 8:
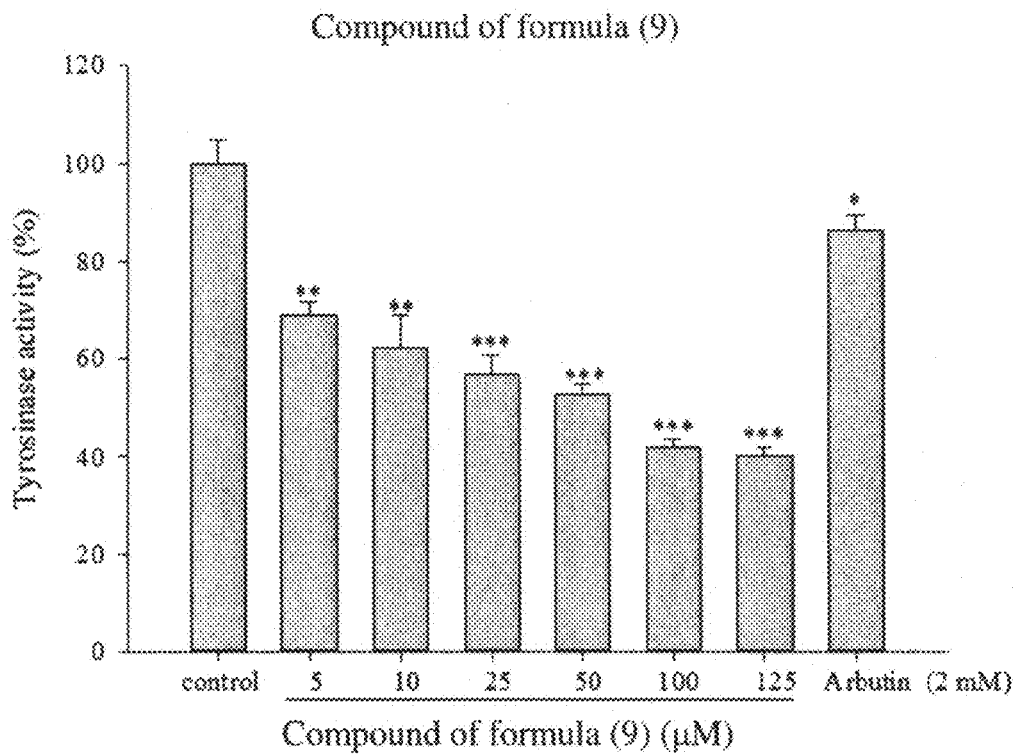
FIGS. 8a and 8b are statistical bar diagrams showing the inhibition of the caffeamide derivatives of the present invention on the activity of tyrosinase in B16 cells.
Figure 8:
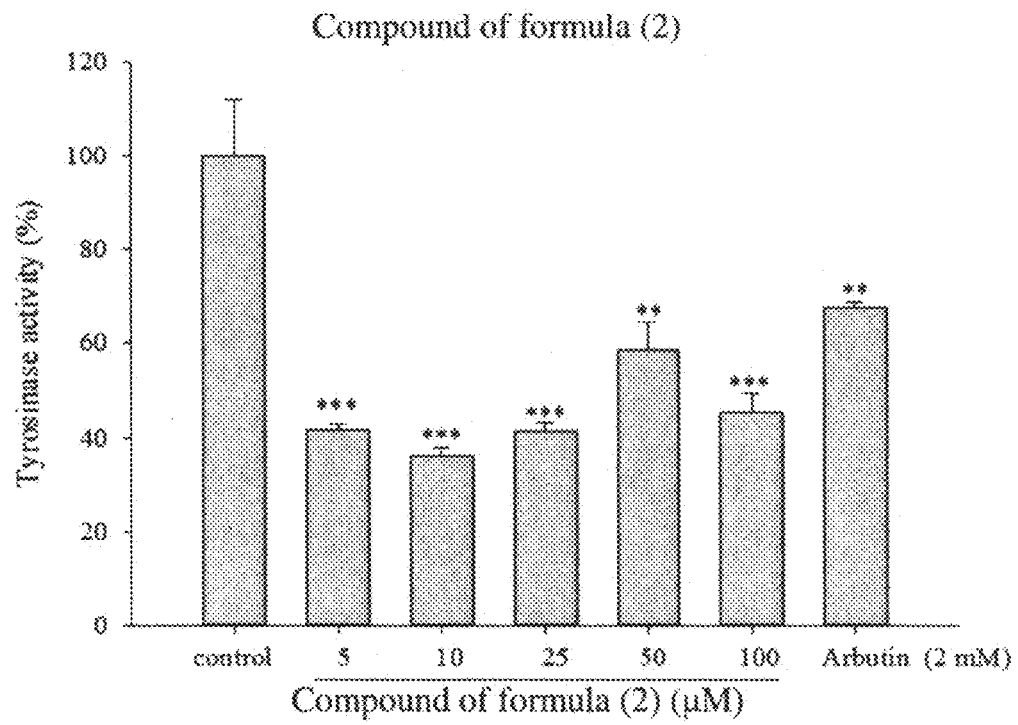
Figure 9:
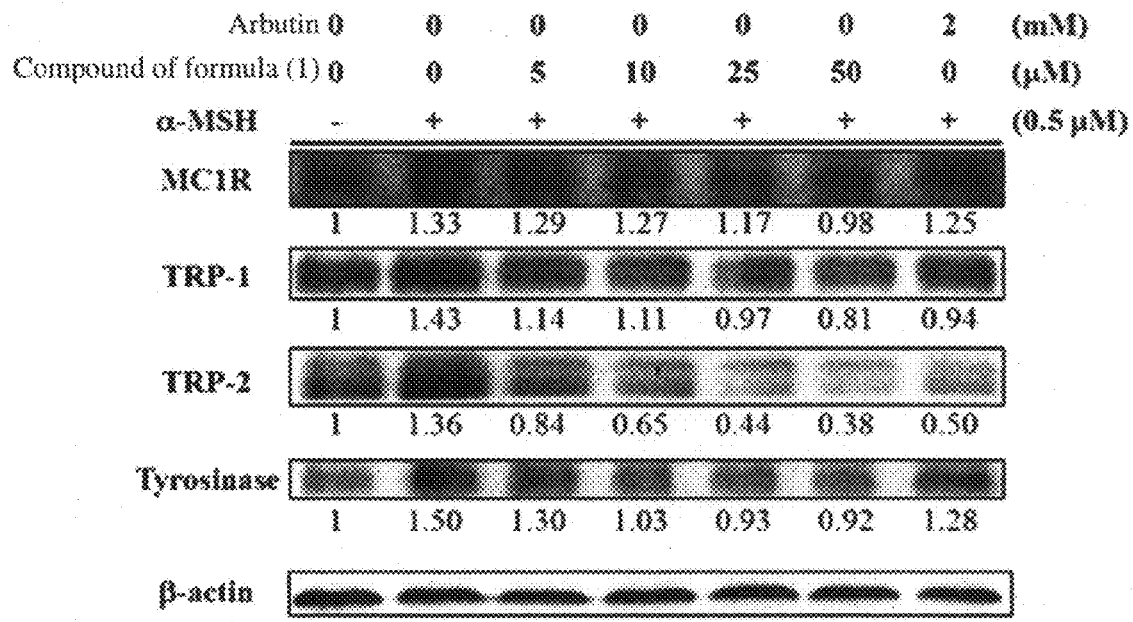
FIGS. 9a to 9d are statistical bar diagrams showing the inhibition of the caffeamide derivatives of the present invention on the expression of melanogenesis pathway-related proteins (MC1R, TRP-1, TRP-2, MITF and tyrosinase) in B16 cells.
Figure 9:
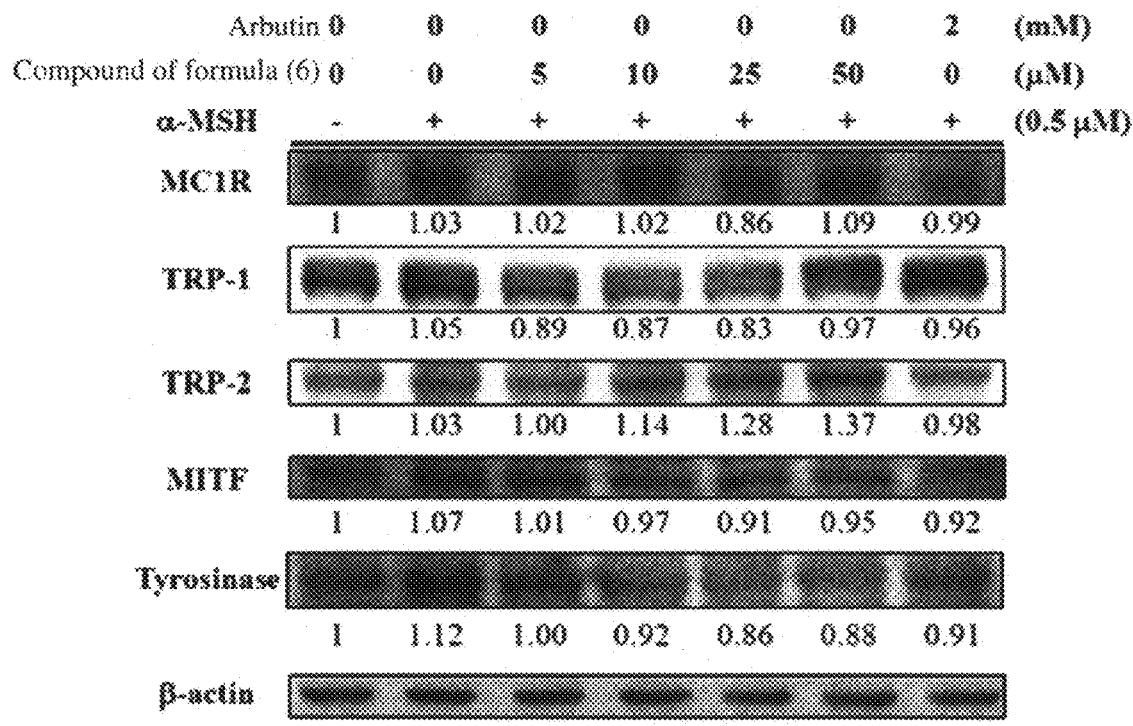
Figure 9:
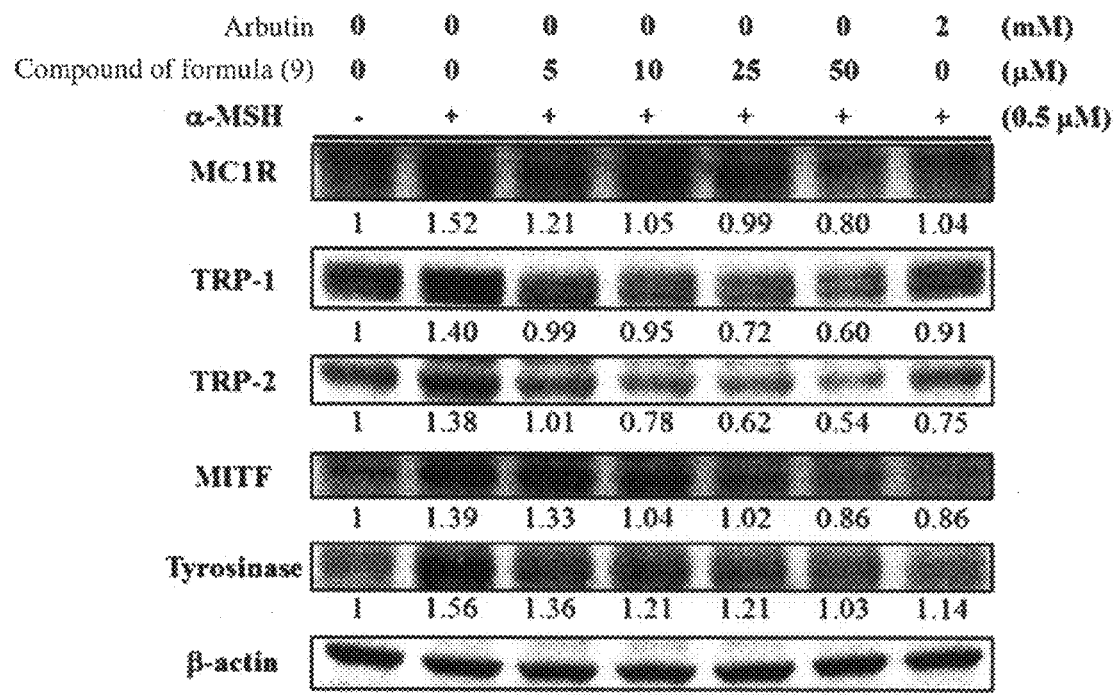
Figure 9:
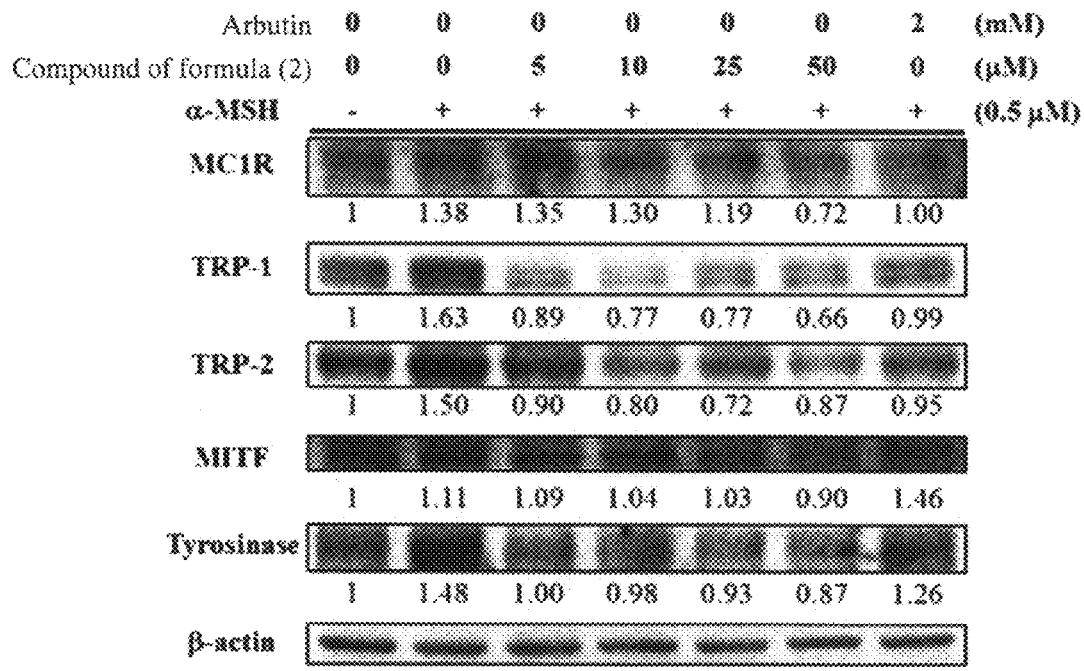

The results in FIG. 8a show that the activity of the tyrosinase in the cells was inhibited after treated with the compound of formula (9) in a concentration dependent way. The results of FIG. 8a show that the activity of the tyrosinase in the cells was inhibited after being treated with the compound of formula (2). The results of this experiment indicate that the caffeamide derivatives described herein can inhibit the formation of melanin by inhibiting the activity of tyrosinase, and provide a benefit of skin whitening.

(3) Expression Analysis of Tyrosinase

It has been know that in addition to tyrosinase, one of the primary proteins participating in melanogenesis, MC1R, TRP-1, TRP-2, and microphthalmia-associated transcription factor (MITF) are also relevant proteins of the melanogenesis pathway. In this experiment, B16 cells (5×10$^5$) were stimulated by α-MSH (0.5 μM) for 24 hours to induce the formation of melanin. Then, the B16 cells stimulated by α-MSH were treated with different concentrations (1 μM to 50 μM) of caffeamide derivatives of formula (1), (6), (9), or (2) prepared in Example 1, respectively, to inhibit the formation of melanin. Next, the content of intracellular MC1R, TRP-1, TRP-2, MITF, tyrosinase were analyzed by western blotting. Arbutin was used as a positive control in this experiment.

FIGS. 9a to 9d show the results of western blotting of the B16 cells treated with the compound of formula (1), (6), (9), or (2). The results of this experiment show that the caffeamide derivatives can inhibit the protein expression levels of MC1R, TRP-1, TRP-2, MITF, and tyrosinase induced by α-MSH in the B16 cells, thereby, inhibiting the formation of melanin.

Example 8

UV Rays Absorbance Test

The compound of formula (1), (6), (9), (2), (8), or (5) (2 mg) prepared in Example 1 was dissolved in 100 ml methanol, respectively. The maximum absorption wavelength (λmax) (nm) of UV rays with a wavelength ranging from 215 nm to 400 nm and the logarithm (log ε) of molar absorption coefficient (ε) of each sample were measured. The results are shown in Table 4.

TABLE 4

| Caffeamide derivative | λmax (logε) |
| --- | --- |
| Compound of formula (1) | 322(4.42); 296(4.36); 245(4.30); 216(4.61) |
| Compound of formula (6) | 324(4.37); 296(4.30); 245(4.28); 215(4.54) |
| Compound of formula (9) | 335(4.59); 295(4.36); 235(4.34) |
| Compound of formula (2) | 322(4.39); 295(4.33); 240(4.36); 219(4.49) |
| Compound of formula (8) | 334(4.18); 295(4.03) |
| Compound of formula (5) | 321(4.16); 295(4.13); 284(4.13); 245(4.16); 225(4.45) |

The results in Table 4 show that the caffeamide derivatives described herein can absorb UV rays with a wavelength ranging from 215 nm to 335 nm and its ε value is larger than 10000 (i.e., the log ε is greater than 3), indicating that the caffeamide derivatives are good UVB blockers.

Example 9

Safety Evaluation Teat (1) Cellular Toxicity Evaluation

MTT (3-(4,5-dimethylthiazol-2-yl)-2,5-diphenyl tetrazolium bromide) assay was used to determine the cellular toxicity of the caffeamide derivatives described herein. First, different concentrations (0 μM to 100 μM) of the compounds of formula (1) or formula (2) prepared in Example 1 of the present invention were added, respectively, into a 96-well microplate which containing human fibroblast Hs68 cells ($1 \times 10^4$ cells per well). After the cells were incubated in an incubator at 37° C. and 5% $CO_2$ for 24 hours, 15 μl of MTT solution (0.5 mg/ml; dissolved in PBS) was added into the microplate and the human fibroblast Hs68 cells were incubated for 3 hours. Next, 75 μl SDS (sodium dodecyl sulfate) solution (10% SDS was dissolved in 0.01N HCl) was added into the microplate. After the cells were maintained for 24 hours, the absorbances of each well were measured at a wavelength of 570 nm by an enzyme immunoassay analyzer. Finally, the cell survival rate was calculated by the following formula to observe the cellular toxicity of compounds. The results are shown in Table 5, FIG. 10a and FIG. 10b.

Cell survival rate(%)=absorbance of the experimental group/absorbance of the control group.

TABLE 5

|  | 0 | 5 | 10 | 25 | 50 |
| --- | --- | --- | --- | --- | --- |
| Compound of formula (1) (μM) |  |  |  |  |  |
| Cell survival rate (%) | 100 ± 7.3 | 99.9 ± 1.8 | 99.5 ± 4.6 | 104.2 ± 3.7 | 107.8 ± 1.2 |
| Compound of formula (2) (μM) |  |  |  |  |  |
| Cell survival rate (%) | 100 ± 1.2 | 92.0 ± 1.0 | 90.4 ± 2.3 | 89.7 ± 2.8 | 86.1 ± 1.4 |

Figure 10:
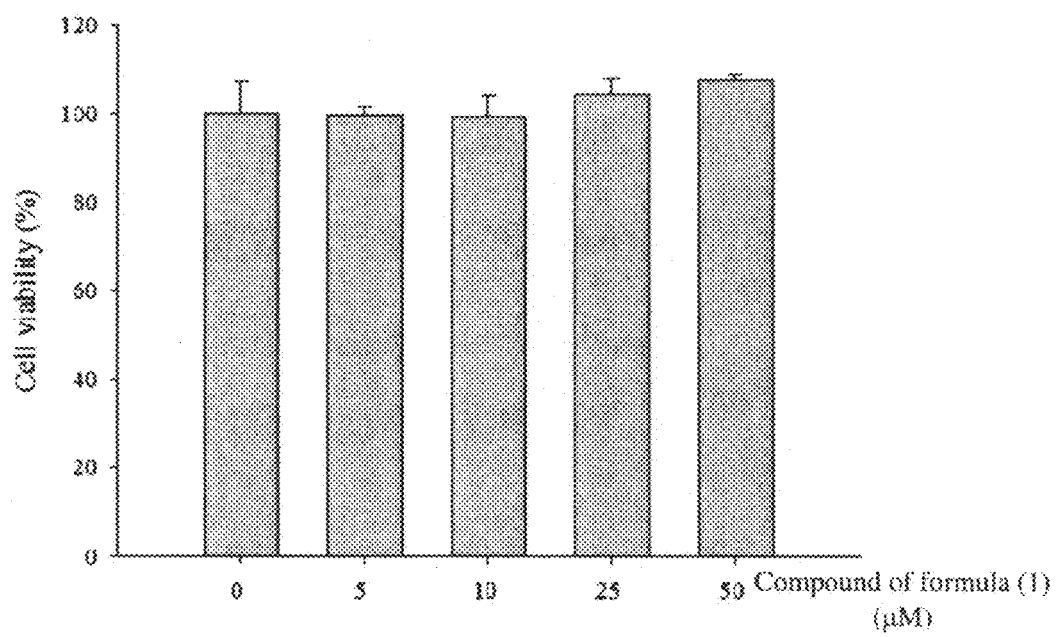
FIGS. 10a and 10b are statistical bar diagrams showing the survival rate of human fibroblast Hs68 cells.
Figure 10:
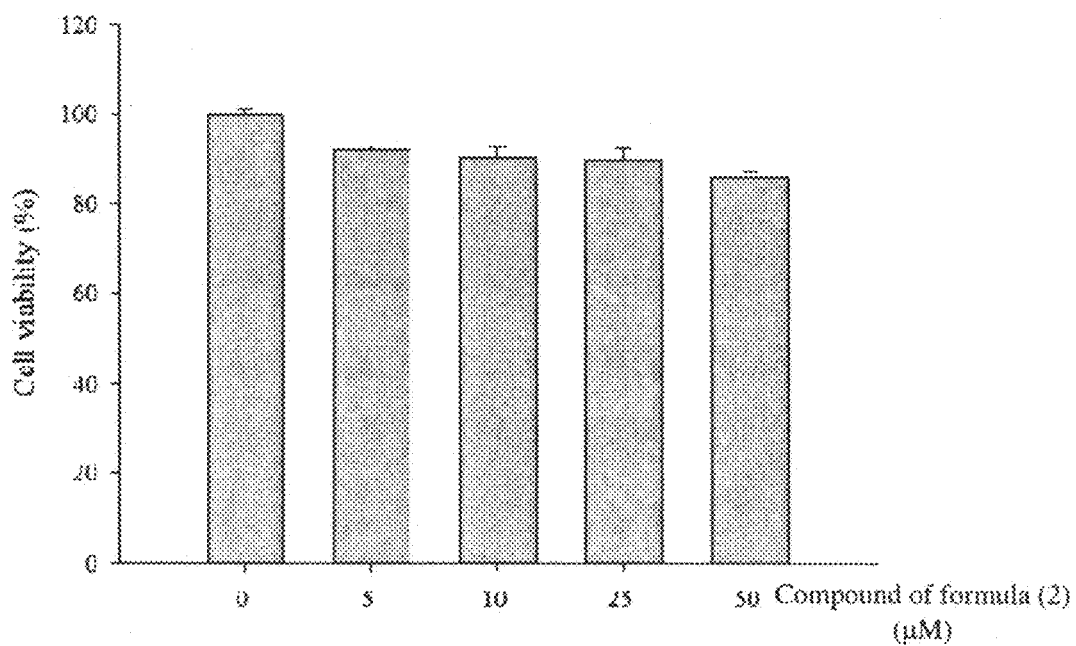
Figure 11:
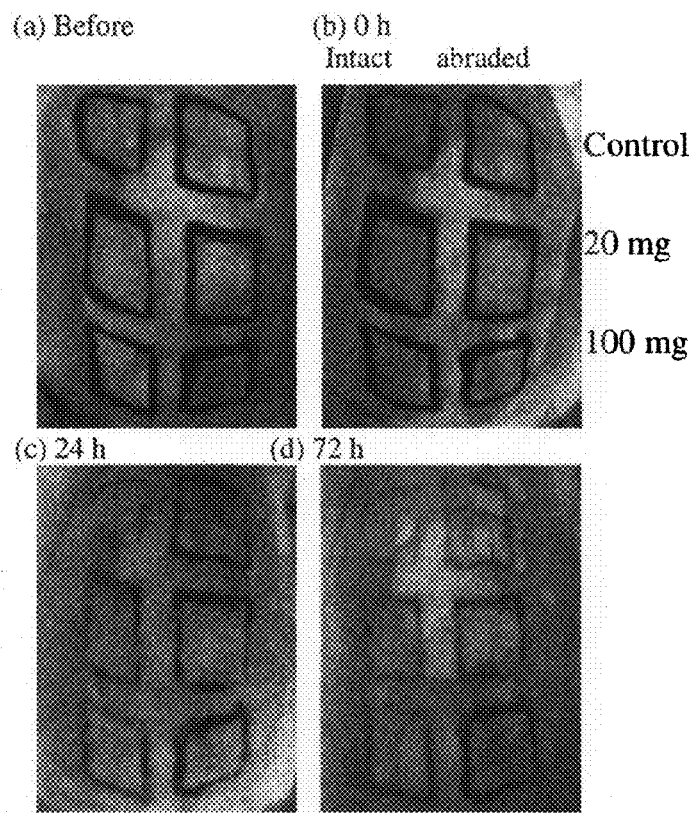
FIGS. 11a 11d are photographs showing the skin variation of the rabbits in the primary skin irritation test.
Figure 12:
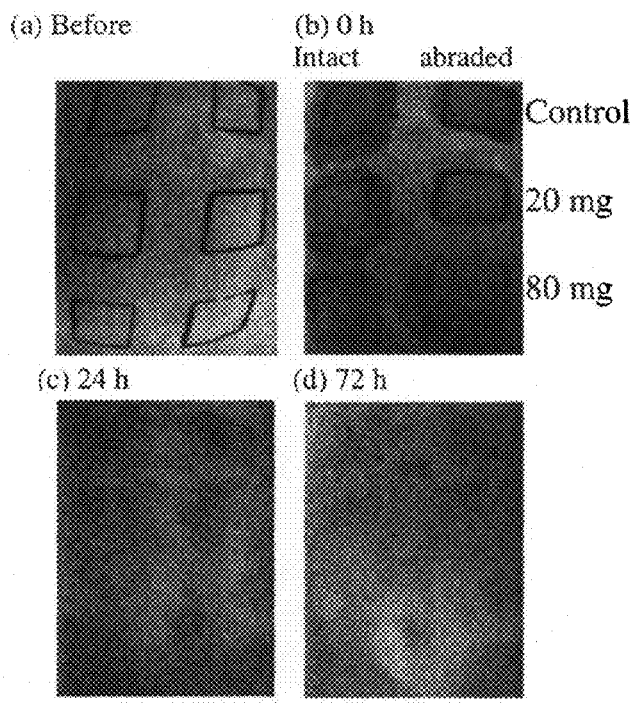
FIGS. 12a to 12d are photographs showing the skin variation of the rabbits in the primary skin irritation test.

As shown in Table 5, FIG. 10a and FIG. 10b, the caffeamide derivatives of the present invention will not cause a cellular toxicity to human fibroblast Hs68 cells even at a high concentration (100 μM). This result of this experiment suggests that caffeamide derivatives described herein have no cellular toxicity to the cells.

(2) Primary Skin Stimulation Test

First, 20 mg (low dosage) and 80 mg or 100 mg (high dosage) of the compounds of formula (1) and formula (2) prepared in Example 1 were dissolved in 1 ml of 40% PEG-400 solution, respectively. Next, a New Zealand white rabbit was fixed on a rabbit cage and the fur on its back was clipped. A color pen was used to draw six squares (2.5 cm×2.5 cm for each square) of smearing region. The six squares were divided into keratin intact group and keratin abraded group. In the keratin abraded group, a sterile needle was used to scrape four parallel lines inside the squares on the back of the white rabbit to damage the keratin layer, but without bleeding. Low dosage and high dosage of compounds of formula (1) or formula (2) were smeared inside the squares evenly. After 24 hours, the skin of white rabbit was wiped with physiologic saline solution to remove compounds of formula (1) or formula (2). The degree of irritation was observed at two time points such as 24 hours and 72 hours respectively and primary irritation index (PII) was determined. The observation time should be extended when the irritation was shown. The degree of irritation and the scale standards for primary irritation index (PII) are shown in Table 6.

The statistical method of this test was analyzed by ANOVA (analysis of variance) and Student's t-test; $p<0.05$ indicates a statistical significance. Each experiment was performed over three times, and the results are shown by the standard error of the mean (mean±standard error). The results are shown in Table 7A, Table 7B, FIGS. 11a to 11d, and FIGS. 12a to 12d.

TABLE 6 scale standards for primary irritation index (PII)

| Irritation response | Primary irritation score |
| --- | --- |
| Erythema and eschar formation | |
| No erythema | 0 |
| Very slight erythema (barely perceptible) | 1 |
| Well-defined erythema | 2 |
| Moderate to severe erythema | 3 |
| Severe erythema (beet-redness) to eschar formation results in the degree that erythema can not be evaluated | 4 |

TABLE 6-continued scale standards for primary irritation index (PII)

| Edema formation | |
| --- | --- |
| No edema | 0 |
| Very slight edema (barely perceptible) | 1 |
| Slight edema (edges of area well-defined by definite raising) | 2 |
| Moderate edema (raised approximately 1.0 mm) | 3 |
| Severe edema (raised more than 1.0 mm and extending beyond exposure area) | 4 |

TABLE 6-continued scale standards for primary irritation index (PII)

Total possible score for irritation: 8

| primary irritation index (PII) | Category of responses |
|---|---|
| 0 | None |
| 0.04~0.99 | Negligible |
| 1.00~1.99 | Very slight |
| 2.00~2.99 | Slight |
| 3.00~5.99 | Moderate |
| 6.00~8.00 | Severe |

TABLE 7A primary irritation index (PII) of the caffeamide derivative of formula (1)

| | | White rabbit number | | | | | | mean ± standard error | |
|---|---|---|---|---|---|---|---|---|---|
| | | 1 | | 2 | | 3 | | | |
| dosage | Time (hour) | Intact* | Abraded* | Intact | abraded | Intact | Abraded | Intact | Abraded |
| Control group | 24 | 0 | 0 | 0 | 0 | 0 | 0 | 0.0 ± 0.0 | 0.0 ± 0.0 |
| | 72 | 0 | 0 | 0 | 0 | 0 | 0 | 0.0 ± 0.0 | 0.0 ± 0.0 |
| 20 mg | 24 | 0 | 0 | 0 | 0 | 0 | 0 | 0.0 ± 0.0 | 0.0 ± 0.0 |
| | 72 | 0 | 0 | 0 | 0 | 0 | 0 | 0.0 ± 0.0 | 0.0 ± 0.0 |
| mg | 24 | 0 | 0 | 0 | 0 | 0 | 0 | 0.0 ± 0.0 | 0.0 ± 0.0 |
| | 72 | 0 | 0 | 0 | 0 | 0 | 0 | 0.0 ± 0.0 | 0.3 ± 0.0 |

*intact: scoring the irritation for intact skin; abraded: scoring the irritation for abraded skin.

TABLE 7B primary irritation index (PII) of the caffeamide derivative of formula (2)

| | | White rabbit number | | | | | | mean ± standard error | |
|---|---|---|---|---|---|---|---|---|---|
| | | 1 | | 2 | | 3 | | | |
| dosage | Time (hour) | Intact | Abraded | Intact | abraded | Intact | Abraded | Intact | Abraded |
| Control group | 24 | 0 | 0 | 0 | 0 | 0 | 0 | 0.0 ± 0.0 | 0.0 ± 0.0 |
| | 72 | 0 | 0 | 0 | 0 | 0 | 0 | 0.0 ± 0.0 | 0.0 ± 0.0 |
| 20 mg | 24 | 0 | 0 | 0 | 0 | 0 | 0 | 0.0 ± 0.0 | 0.0 ± 0.0 |
| | 72 | 0 | 0 | 0 | 0 | 0 | 0 | 0.0 ± 0.0 | 0.0 ± 0.0 |
| 80 mg | 24 | 0 | 0 | 0 | 1 | 0 | 1 | 0.0 ± 0.0 | 0.7 ± 0.6 |
| | 72 | 0 | 0 | 0 | 0 | 0 | 1 | 0.0 ± 0.0 | 0.3 ± 0.6 |

As shown in Table 7A, Table 7B, FIGS. 11a to 11d, and FIGS. 12a to 12d, after the rabbits were treated for 24 hours or 72 hours, the caffeamide derivatives described herein do not cause any irritation on the intact or abraded skin without respect to be treated with low dosage (20 mg) or high (80 mg or 100 mg). The primary irritation index (PII) of the caffeamide derivatives are all "0.0", which belongs to the irritation range of "non-irritation." The results of this test show that the caffeamide derivatives described herein do not have irritation to skin.

The results in the above examples show that the caffeamide derivatives described herein have the effects of anti-oxidation, inhibiting the activity and/or expression of MMPs, inhibiting the phosphorylation of MAPK, promoting the expression of collagen, inhibiting the activity and/or expression of tyrosinase, inhibiting the expression of tyrosinase related protein-1 and/or tyrosinase related protein-2, and/or absorbing UV rays with a wavelength ranging from 210 nm to 400 nm, and thus, can be used for improving, caring, and/or repairing the skin, anti-skin aging, especially for anti-skin photo-aging and whitening the skin.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for anti-skin aging in a subject, comprising administering to the subject in need thereof an effective amount of an active component selected from the group consisting of the following compounds:

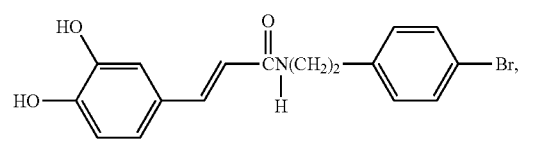

(2)

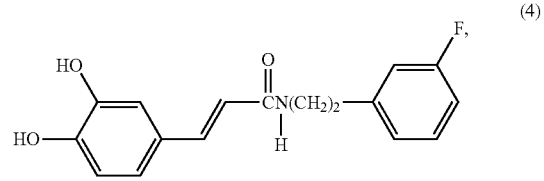

(4)

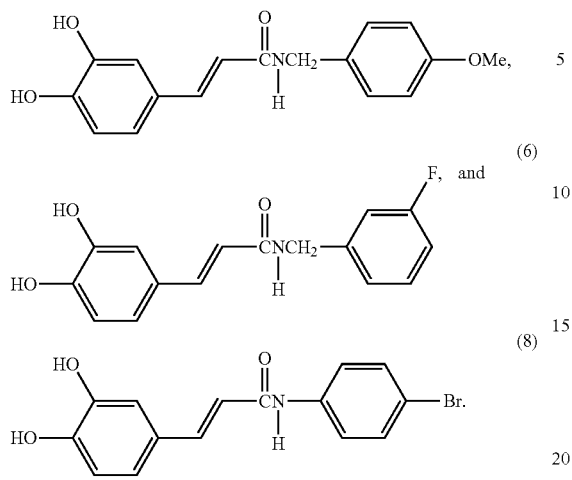

2. The method as claimed in claim 1, wherein the method is for anti-skin photo-aging.

3. The method as claimed in claim 1, wherein the method is for anti-oxidation, inhibiting the activity and/or expression of MMP-1, MMP-3, and MMP-9, inhibiting the phosphorylation of mitogen-activated protein kinase (MAPK), promoting the expression of collagen, inhibiting the activity and/or expression of tyrosinase, inhibiting the expression of tyrosinase related protein-1 and/or tyrosinase related protein-2, and/or absorbing ultraviolet (UV) rays with a wavelength ranging from 210 nm to 400 nm.

4. The method as claimed in claim 3, wherein the method is for promoting the expression of Type I collagen and/or inhibiting the expression of melanin.

5. The method as claimed in claim 3, wherein the method is for absorbing ultraviolet (UV) rays with a wavelength ranging from 280 nm to 335 nm.

6. A method for improving, repairing, and/or caring the skin of a subject, comprising administering to the subject in need thereof an effective amount of an active component selected from the group consisting of the following compounds:

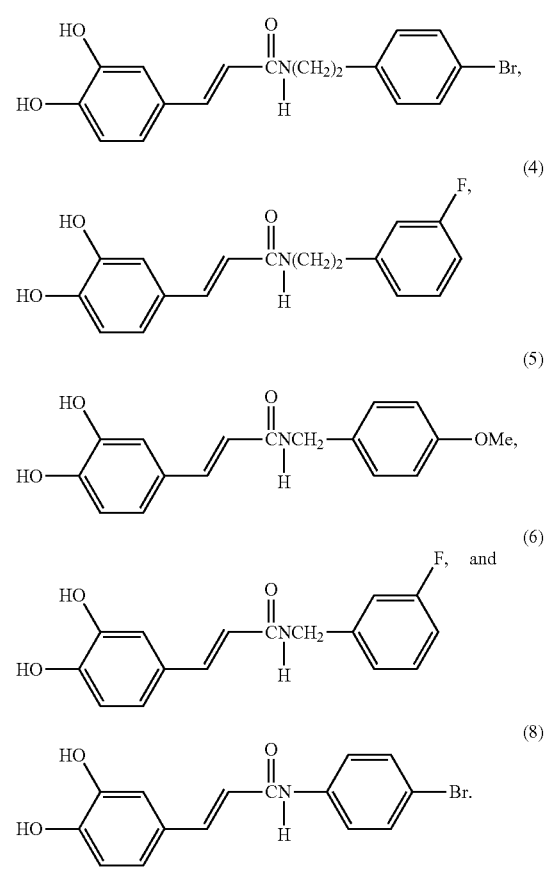

7. The method as claimed in claim 6, wherein the method is for anti-skin photo-aging and/or whitening skin.

8. The method as claimed in claim 6, wherein the method is for reducing skin wrinkling and improving skin quality and skin flaccidity.

* * * * *